(12) United States Patent
Haixiang (10) Patent No.: US 7,838,017 B2
(45) Date of Patent: *Nov. 23, 2010

(54) POLYINOSINIC ACID-POLYCYTIDYLIC ACID-BASED ADJUVANT

(75) Inventor: Lin Haixiang, Fangxingyuan (CN)

(73) Assignee: Newbiomed Pika Pte Ltd, Singapore (SG)

( * ) Notice: Subject to any disclaimer, the term of this patent is extended or adjusted under 35 U.S.C. 154(b) by 282 days.

This patent is subject to a terminal disclaimer.

(21) Appl. No.: 10/551,847

(22) PCT Filed: Jun. 8, 2005

(86) PCT No.: PCT/CN2005/000810

§ 371 (c)(1),
(2), (4) Date: Jun. 23, 2006

(87) PCT Pub. No.: WO2006/131023

PCT Pub. Date: Dec. 14, 2006

(65) Prior Publication Data

US 2007/0160632 A1    Jul. 12, 2007

(51) Int. Cl.
*A61K 47/00* (2006.01)
(52) U.S. Cl. .................................. 424/278.1
(58) Field of Classification Search ........................ None
See application file for complete search history.

(56) References Cited

U.S. PATENT DOCUMENTS

| | | | |
|---|---|---|---|
| 3,666,646 A | 5/1972 | Lampson et al. | |
| 3,692,899 A | 9/1972 | Levy | |
| 3,906,092 A | 9/1975 | Hilleman et al. | |
| 3,952,097 A | 4/1976 | Levy | |
| 4,024,241 A | 5/1977 | Levy | |
| 4,082,735 A | 4/1978 | Jones et al. | |
| 4,082,736 A | 4/1978 | Jones et al. | |
| 4,094,971 A | 6/1978 | Chedid et al. | |
| 4,101,536 A | 7/1978 | Yamamura et al. | |
| 4,124,702 A | 11/1978 | Lampson et al. | |
| 4,140,761 A | 2/1979 | Gerin et al. | |
| 4,153,684 A | 5/1979 | Audibert et al. | |
| 4,185,089 A | 1/1980 | Derrien et al. | |
| 4,186,194 A | 1/1980 | Adam et al. | |
| 4,235,771 A | 11/1980 | Adam et al. | |
| 4,314,998 A | 2/1982 | Yamamura et al. | |
| 4,323,559 A | 4/1982 | Audibert et al. | |
| 4,327,085 A | 4/1982 | Audibert et al. | |
| 4,349,538 A | 9/1982 | Levy | |
| 4,369,178 A | 1/1983 | Yamamura et al. | |
| 4,389,395 A | 6/1983 | Lerner et al. | |
| 4,954,298 A | 9/1990 | Yamamoto et al. | |
| 6,468,558 B2 | 10/2002 | Wong | |
| 2007/0166239 A1 | 7/2007 | Lin | |
| 2007/0166800 A1 | 7/2007 | Lin | |

FOREIGN PATENT DOCUMENTS

| | | |
|---|---|---|
| CN | 1095951 | 12/1994 |
| CN | 93105862.7 | 9/2000 |
| EP | 0025766 A2 | 3/1981 |
| EP | 0025766 A3 | 3/1981 |
| FR | 2476488 A2 | 8/1981 |
| JP | 57002220 | 1/1982 |
| JP | 01093540 A2 | 4/1989 |
| JP | 1186818 | 7/1989 |
| WO | WO 2005/014038 | 2/2005 |

OTHER PUBLICATIONS

Lin et al. A new immunostimulatory complex PICKCa in experimental rabies: antiviral and adjvuant effects. Archives of Virology, vol. 131, Nos. 3-4, Sep. 1993, 307-319.*
Morahan et al. Antiviral activity and side effects of polyriboinosinic-cytidylic acid complexes as affected by molecular size. Proc. Nat. Acad. Sci., USA, Apr. 1972, vol. 69, No. 4, 842-846.*
Zong et al. Study on determining the molecular weight of PICKCa and PI,PC with the method of polyacrylamide gel electrophoresis. Chinese Journal of Pharmaceutical Analysis. 1993, vol. 13, No. 4, pp. 219-222.*
Hu, Q.G. Basic Research on Poly I:C (review). Chinese Medical and Pharmaceutical Industry Journal. 1983, (9) 3134. (With English Abstract).
Hu, Q.G. Tianjin Poly I:C Laboratory Research and Clinical Application. Fujian Medical Journal. 1983, vol. 12, No. 6, pp. 31-34. (With English Abstract).
Zong, J., et al. Study on Determining the Molecular Weight of PICKCa and PI, PC with the Method of Polyacrylamide Gel Electrophoresis. Chinese Journal of Pharmaceutical Analysis. 1993, vol. 13, No. 4, pp. 219-222. (With English Abstract).
Houston et al. "Modified Polyriboinosinic-Polyribocytidylic Acid, an Immunological Adjuvant," Infection and Immunity, American Society for Microbiology, Jul. 1976, vol. 14(1) p. 318-319.
Kende et al. "Enhanced Therapeutic Efficacy of Poly(ICLC) and Ribavirin Combinations against Rift Valley Fever Virus Infection in Mice," Antimicrobial Agents and Chemotherapy, American Society for Microbiology, Jul. 1987, vol. 31(7) p. 986-990.
Lake et al. Involvement of protein kinase C in macrophages activation by poly (C). American Journal of Physiology (1994) vol. 266(1) pp. C134-C142.

(Continued)

*Primary Examiner*—Emily M. Le
(74) *Attorney, Agent, or Firm*—Carol L. Francis; Bozicevic, Field & Francis LLP (57) ABSTRACT

The present invention provides a polynucleotide adjuvant composition and methods of use in eliciting an immune response. The present invention also provides an immunogenic composition comprising the polynucleotide adjuvant composition together with an antigen (e.g., as in a vaccine). The adjuvant compositions of the invention have particular physical properties (e.g., molecular weight, concentration, and pH) which address the need for a safe adjuvant for eliciting an enhanced immune response. The present invention further contemplates methods of use of such adjuvant compositions, particularly in eliciting an immune response to an antigenic compound.

38 Claims, 1 Drawing Sheet

OTHER PUBLICATIONS

Levy et al. "Immune Modulating Effects of Poly ICLC," Annals New York Academy of Sciences, 1980, p. 33-41.

Lin et al. A new immunostimulatory complex (PICKCa) in experimental rabies: antiviral and adjuvant effects. Archives of Virology (1993) col. 131: pp. 307-319.

Ellouz, F., et al. Minimal structural requirements for adjuvant activity of bacterial peptidoglycan derivatives. Biochemical and Biophysical Research Communications. 1974, vol. 59, No. 4, pp. 1317-1325.

Gupta, R. K., et al. Adjuvants for human vaccines—current status, problems and future prospects. Vaccine. 1995, vol. 13, No. 14, pp. 1263-1278.

Gupta, R. K., et al. Adjuvants—a balance between toxicity and adjuvanticity. Vaccine. 1993, vol. 11, pp. 293-306.

Kanzler, H., et al. Therapeutic targeting of innate immunity with toll-like receptor agonists and antagonists. Nature Medicine. 2007, vol. 13, No. 5, pp. 552-559. E-pub May 3, 2007.

Kenney, R. T., et al. Meeting report, 2nd meeting on novel adjuvants currently in/close to human clinical testing, World Health Organization—Organization Mondiale de la Sante, Fondation Merieux, Annecy, France, Jun. 5-7, 2000. Vaccine. 2002, vol. 20, pp. 2155-2163.

Morahan, P. S., et al. Antiviral activity and side effects of polyriboinosinic-cytidylic acid complexes as affected by molecular size. Proceedings of the National Academy of Sciences USA. 1972, vol. 69, No. 4, pp. 842-846.

Norlund, J. J., et al. Inhibition of biologic activity of Poly I: Poly C by human plasma (34492). Proc Soc Exp Biol Med. 1970, vol. 133, pp. 439-444.

Phillips, B. M., et al. Systemic toxicity of polyinosinic acid: polycytidylic acid in rodents and dogs. Toxicology and Applied Pharmacology. 1971, vol. 18, pp. 220-230.

Sela, M. Antigenicity: some molecular aspects. Science. 1969, vol. 166, pp. 1365-1374.

Stern, R. A nuclease from animal serum which hydrolyzes double-stranded RNA. Biochemical and Biophysical Research Communications. 1970, vol. 41, No. 3, pp. 608-614.

Wright, C. L., et al. The adjuvant effects mycoviral dsRNA and polyinosinic:polycytidylic acid on the murine immune response. Biochemical and Biophysical Research Communications. 1985, vol. 131, No. 2, pp. 949-955.

Lin; et al., "A new immunostimulatory complex (PICKCa) in experimental rabies: antiviral and adjuvant effects", Archives of Virology (1993), 131(3-4):307-19.

Lin; et al., "Experimental Study of Rabies Vaccine Plus Pika Adjuvant", Chinese Journal of Biologicals (1998), 11(3):4 pages, Translated by Schreiber Translations, Inc. (2008).

Zong; et al., "Study on Determining the Molecular Weight of PICKCa and PI. PC with the Method of Polyacrylamide Gel Electrophoresis(PAGE)", Chinese Journal of Pharmaceutical Analysis (1993), 13:s219-222, English translation.

Zong Jianchao et al.(1993) "Study on Determining the Molecular Weight of PICKCa and PI.PC with the Method of Polyacrylamide Gel Electrophoresis (PAGE)" Chinese Journal of Pharm. Analysis 13 (4): 219-222 (with English Translation).

Champney, et al., Modified polyriboinosinic-polyribocytidylic acid complex: sustained interferonemia and its physiological associates in humans, Infect Immun. Sep. 1979; 25(3): 831-837.

De Clercq, Degradation of Poly(inosinic acid) • poly(cytidylic acid) [(I)n• (Cn)] by Human Plasma, European Journal of Biochemistry, vol. 93 Issue 1, pp. 165-172, Jun. 28, 2008.

Gatmaitan, et al., Modified Polyriboinosiniic-Polyribocytidylic Acid Complex: Induction of Serum Interferon, Fever, and Hypotension in. Rabbits, Antimicrobial agents and chemotherapy, Jan. 1980, p. 49-54, vol. 17. No. 1.

Levy, et al., Interferon induction in primates by stabilized polyriboinosinic acid-polyribocytidylic acid: effect of component size, Infect Immun. Nov. 1981; 34(2): 416-421.

Machida, et al., Relationship between the molecular size of poly I-poly C and its biological activity, Jpn J Microbiol. Apr. 1976;20(2):71-76.

Shu, et al., Biological function and application of Poly I:C, the First Affiliated Hospital of Xian Medical College, Shanxi Journal of Medicine, 1989, 18(10), 40-42.

Smorodintsev, et al., Comparative study of the toxicity of poly G-poly C and poly I-poly C in different objects, Vopr Virusol. Mar.-Apr. 1978;(2):201-206.

Stringfellow, et al., Interferon induction by and toxicity of polyriboinosinic acid [poly(rI)].polyribocytidylic acid [poly(rC)], mismatched analog poly (rI).poly[r(C12Uracil)n], and poly(rI).poly(rC) L-lysine complexed with carboxymethylcellulose, Antimicrob Agents Chemother. Jun. 1980; 17(6): 988-992.

Ts'O, et al., An Integrated and Comparative Study of the Antiviral Effects and Other Biological Properties of the Polyinosinic Acid-Polycytidylic Acid and Its Mismatched Analogues, Molecular Pharmacology, vol. 12, 299-312, Copyright 1976 by the American Society for Pharmacology and Experimental Therapeutics.

US 6,008,200, 12/1999, Krieg et al. (withdrawn)

* cited by examiner

Figure 1

1. 100bp DNA Marker
2. PIKA 20000304
3. PIKA 20000304 + IPRV
4. IPRV antigen
5. Av-PICKCa 000703
6. Av-PICKCa 000703 + IPRV

Figure 2

In-Vitro Interferon-gamma Production

US 7,838,017 B2

POLYINOSINIC ACID-POLYCYTIDYLIC ACID-BASED ADJUVANT

FIELD OF INVENTION

The invention generally relates to adjuvant compositions and methods of their use in enhancing an immune response, more particularly to compounds, vaccines and methods for enhancing the immunogenicity of an antigen, and more particularly to polynucleotide adjuvant compositions, vaccines comprising the polynucleotide adjuvant compositions, and methods of using said polynucleotide adjuvant compositions and vaccines to enhance immune responses in a host.

BACKGROUND OF INVENTION

Description of Related Art

The immune system may exhibit both specific and nonspecific immunity. Generally, B and T lymphocytes, which display specific receptors on their cell surface for a given antigen, produce specific immunity. The immune system may respond to different antigens in two ways: 1) humoral-mediated immunity, which includes B cell stimulation and production of antibodies or immunoglobulins, antigen-presenting cells (APCs), and helper T cells (Th1 and Th2), and 2) cell-mediated immunity (CMI), which generally involves T cells including cytotoxic T lymphocytes (CTLs), although other cells are also involved in the generation of a CTL response (e.g., Th1 and/or Th2 cells and APCs).

Nonspecific immunity encompasses various cells and mechanisms such as phagocytosis (the engulfing of foreign particles or antigens) by macrophages or granulocytes, and natural killer (NK) cell activity, among others. Nonspecific immunity relies on mechanisms less evolutionarily advanced and does not display the acquired nature of specificity and memory, which are exemplary hallmarks of a specific immune response. The key differences between specific and nonspecific immunity are based upon B and T cell specificity. These cells predominantly acquire their responsiveness after activation with a specific antigen and have mechanisms to display memory in the event of future exposure to that specific antigen. As a result, vaccination (involving specificity and memory) is an effective protocol to protect against harmful pathogens.

Adjuvants are generally compounds, that when administered with an antigen (either mixed with, or given prior to the administration of the antigen) enhances or modifies the immune response to that particular antigen.

Exemplary adjuvants that have been used to enhance an immune response include aluminum compounds (all generally referred to as "Alum"), oil-in-water emulsions (complete Freund's adjuvant (CFA) is an oil-in-water emulsion containing dried, heat-killed *Mycobacterium tuberculosis* organisms), Saponin (isolated from the bark of *Quillaja Saponoria*, the adjuvant active component known as Quile A), CpG ODN (synthetic oligodeoxynucleotide containing unmethylated CpG dinucleotides), MPL (derived from the lipopolysaccharide of *Salmonella minnesota* Re595), Liposomes (usually made up of biodegradable materials such as phospholipids) and Biodegradable polymer microspheres (made from a variety of polymers such as PLGA, polyphosphazene and polyanhydrides). The adjuvant properties of these compounds have been evaluated with each adjuvant showing advantages and disadvantages.

The biggest issue with the use of adjuvants for human vaccines, particularly routine childhood vaccines, is the toxicity and adverse side-effects of most of the adjuvant formulations. The application of new technologies to vaccine development is leading to purified, subunit and synthetic antigens, which tend to have poor immunogenicity. The development of new adjuvants, to improve immunogenicity/efficacy and reduce side effects, presents one of the major challenges of vaccine research and development.

Polynucleotide complexes have been investigated for their various applications including acting as adjuvants. Double-stranded RNAs (dsRNAs) are very potent biologic modifiers that can exert a profound influence on cells at nanomolar concentrations. The modulating effects of dsRNA include a broad spectrum of actions at the molecular and cellular levels. At the molecular level, dsRNAs can elicit; biological effects such as interferon synthesis, induction of protein kinase, enhancement of histocompatibility antigen and inhibition of metabolism. And at the cellular level, dsRNA can elicit biological effects such as pyrogenicity, mitogenicity, macrophage activation, activation of cell-mediated immunity and induction of antiviral state. One promising potential of dsRNAs is its immunomodulating effect in antimicrobial therapies. U.S. Pat. No. 4,124,702 disclosed that double stranded polynucleotides induced interferon induction in living animal cells. U.S. Pat. No. 3,906,092 disclosed that the antibody response to an adjuvant type vaccine was augmented by incorporation in the vaccine of a polynucleotide or a complex of polynucleotides. Houston et al. established PICLC (polyinosinic acid polycytidylic acid poly-L-lysinecarboxy-moethylcellulose complex) as a potent adjuvant by increasing primary antibody response without the aid of an additional adjuvant. Houston et al., Infection and Immunity, 14: 318-9, 1976C. Mycoviral dsRNA was found to enhance significantly the hemagglutinating antibody response to sheep red blood cells (sRBC). Wright and Adler-Moore, Biochemical and Biophysical Research Communications, 131: 949-45, 1985.

However, PIC (polyinosinic acid polycytidylic acid) manifests severe toxicity when used in animals. For example, Phillips et al. reported that severe toxic manifestations were elicited in dogs upon the sub-chronic administration of PIC at a dose of 2.0 mg/kg. Toxicity was characterized by decreased spontaneous activity, poor co-ordination, vomiting, anorexia, weight loss, hematologic changes reflecting decreased hematopoiesis, increased alkaline phosphatase and transaminase activities, thymus degeneration, destruction of bone marrow, dilatation of hepatic sinusoidal capillaries in the centrolobular areas, necrosis of liver cells, collapse of hepatic structures, and a generalized arthritis. See, Phillips et al., Toxicology and Applied Pharmacology, 18: 220-30, 1971.

PIC, one of most studied polynucleotide complexes, was not effective when used in monkeys and humans due to its instability in the body after administration. Thus, PIC has been modified in many ways to overcome one or another deficiency. For example, a complex of polyriboinosinic-polyribocytidylic acid with poly-L-lysine hydrobromide is about 5 to 15 times as resistant to hydrolysis by pancreatic ribonuclease as the parent PIC. Another example is the dsRNA polyICLC, or PICLC for short, that was found highly effective as an antiviral or antitumor agent. PICLC is a synthetic dsRNA composed of polyriboinosinic and polyribocytidylic acid strands (PIC). Although PICLC is a promising immunomodulator which has great potential in antimicrobial and anticancer therapies, it has been shown to produce serious side effects in humans, especially when the drug is administered in multiple high doses. Some of the reported side effects include fever, hypotension, leukopenia, myalgia, thrombocytopenia and polyarthalgia. The inherent toxicity problem must be overcome to render PICLC safe for use in humans. Furthermore, the therapeutic efficacy of poly ICLC is limited by its stability in vivo.

An antiviral drug composed of polyinosinic acid-polycytidylic acid (Poly I:C), kanamycin and calcium (Av-PICKCa) is used for treating viral infections. Av-PICKCa has been shown to be able to induce interferon and interleukin-2 production. Av-PICKCa administered alone as an antiviral drug stimulates a non-specific immune response, i.e., stimulates a form of interferon that is not specific to any particular antigen. This anti-viral response is profoundly different from the antigen-specific immune response generated when an adjuvant is administered in conjunction with an antigen.

More importantly, the inventor of the present invention discovered that Av-PICKCa had the properties of an adjuvant, i.e., the ability to elicit a specific immune response when administered with an antigen. Further, the inventor further discovered that Av-PICKCa was an effective adjuvant when used together with rabies and hemorrhagic fever antigens.

Lin et al. described that Av-PICKCa can be used as an adjuvant (Lin, et al., A new immunostimulatory complex (PICKCa) in experimental rabies: antiviral and adjuvant effects, Arch Virol, 131: 307-19, 1993; and Chinese Patent No. 93105862.7). The Chinese Patent No. 93105862.7 provides for the use of the general composition of Poly I:C, kanamycin and calcium (PICKCa) as an adjuvant in a vaccine for human and mammalian application.

Samples of Av-PICKCa are heterogeneous with respect to size and weight of the molecules. Av-PICKCa is described in the literature in terms of an average or range of sedimentation co-efficient values as measured by Svedbergs S. The antiviral drug Av-PICKCa exists in one embodiment from 5 S to 8 S (Source A) see, Zhung J. C., Research recollection of polyinosinic-polycytidylic acid (PIC). The paper of fifth Chinese interferon conference in clinical application and theory, Siam 1985, pp 23-28. In other embodiments Av-PICKCa exists with a sedimentation co-efficient of 4 S to 12 S with an average of 6 S (Source B) or 5 S to 12 S with an average of 7 S (Source C) or 8 S to 10 S (Source D) see Hu Q. G., Tianjin Av-PICKCa's laboratory research and clinical application, Fujian Medical Journal, 1983.12; (6): 28-30 and Hu Q. G. Chinese Medical and Pharmaceutical Industry Journal, 1983 (9) 3134.

The sedimentation co-efficient of this heterogeneous collection of molecules in Av-PICKCa is convertible to an equivalent molecular weight (mw in Daltons) using the conversion formula $mw=1,100 \times S^{2.2}$ (see Su B. X. et al; Introduction of Biochemical Technology, 1$^{st}$ Edition, Zhongshan University, 1978, 356-357). The results of the conversion into Daltons are presented in the table below:

TABLE A

Characteristics of Av-PICKCa

| Av-PICKCa | Sedimentation Co-efficient S | | | Molecular Weight Daltons | | |
|---|---|---|---|---|---|---|
| Source | Min. | Max. | Avg. | Min. | Max. | Avg. |
| A | 5 | 8 | * | 38,000 | 107,000 | * |
| B | 4 | 12 | 6 | 23,000 | 260,000 | 57,000 |
| C | 5 | 12 | 7 | 38,000 | 260,000 | 79,000 |
| D | 8 | 10 | * | 107,000 | 174,000 | * |

* data not cited in reference

The original research on Av-PICKCa as an adjuvant by Lin et al. was with a sample having molecules that had similar characteristics to Source A, i.e., a sedimentation co-efficient of 5 S to 8 S, that is an equivalent molecular weight of molecules ranging from 38,000 Daltons to 107,000 Daltons. (see Lin et al., supra).

All forms of PICKCa were believed to be equally safe and effective given that Av-PICKCa is essentially a form of PICKCa and further given the historical use of Av-PICKCa as an antiviral drug. However, this proved not to be the case. Research conducted by the inventor demonstrates that the efficacy and toxicity of PICKCa, when used as an adjuvant in combination with an antigen, actually vary with different molecular weights. The inventor found that Av-PICKCa does not provide the optimal efficacy/safety profile for use as an adjuvant and that PICKCa does induce unacceptable adverse side effects under certain conditions. Thus there remains a need for an adjuvant which is more suitable for human use and which is safe and effective in providing the desired immunogenic effect. The current invention addresses this need and provides other advantages that will be apparent with reference to the detailed description.

LITERATURE

The following references may be of interest:
JP 1093540A2;
U.S. Pat. No. 4,124,702
U.S. Pat. No. 3,692,899
U.S. Pat. No. 3,906,092
U.S. Pat. No. 4,389,395
U.S. Pat. No. 4,349,538
U.S. Pat. No. 4,024,241
U.S. Pat. No. 3,952,097
Houston et al., Infection and Immunity, 14: 318-9, 1976C
Wright and Adler-Moore, Biochemical and Biophysical Research Communications, 131: 949-45, 1985
Phillips et al., Toxicology and Applied Pharmacology, 18: 220-30, 1971
Lin, et al., A new immunostimulatory complex (PICKCa) in experimental rabies: antiviral and adjuvant effects, Arch Virol, 131: 307-19, 1993
China Patent 93105862.7
Zhung J. C., Research recollection of polyinosinic-polycytidylic acid (PIC). The paper of fifth Chinese interferon conference in clinical application and theory, Siam 1985, pp 23-28
Hu Q. G., Tianjin Av-PICKCa's laboratory research and clinical application, Fujian Medical Journal, 1983.12; (6): 28-30
Hu Q. G. Chinese Medical and Pharmaceutical Industry Journal, 1983 (9) 3134.
Su B. X. et al; Introduction of Biochemical Technology, 1$^{st}$ Edition, Zhongshan University, 1978, 356-357
Gupta R. K. et al., Adjuvants—a balance between toxicity and adjuvanticity, Vaccine, 11:293-306, 1993
Arnon, R. (Ed.) Synthetic Vaccines 1:83-92, CRC Press, Inc., Boca Raton, Fla., 1987
Sela, M., Science 166:1365-1374 (1969)
U.S. Pat. No. 6,008,200
Ellouz et al., Biochem. & Biophy. Res. Comm., 59:1317, 1974
U.S. Pat. No. 4,094,971
U.S. Pat. No. 4,101,536
U.S. Pat. No. 4,153,684
U.S. Pat. No. 4,235,771
U.S. Pat. No. 4,323,559
U.S. Pat. No. 4,327,085
U.S. Pat. No. 4,185,089
U.S. Pat. No. 4,082,736

U.S. Pat. No. 4,369,178
U.S. Pat. No. 4,314,998
U.S. Pat. No. 4,082,735
U.S. Pat. No. 4,186,194
U.S. Pat. No. 6,468,558
New Trends and Developments in Vaccines, edited by Voller et al., University Park Press, Baltimore, Md., USA, 1978
Klein, J., et al., Immunology (2nd), Blackwell Science Inc., Boston (1997)
Gupa R. K. and Siber G. R., Adjuvants for human vaccines—current status, problems and future prospects, Vaccine, 13 (14): 1263-1276, 1995
Richard T Kenney et al. Meeting Report—$2^{nd}$ meeting on novel adjuvants currently in/close to human clinical testing, Vaccine 20 2155-2163, 2002
Laboratory Techniques in Rabies Edited by F X Meslin, M M Kaplan, H Koprowski $4^{th}$ Edition ISBN 92 4 1544 1

SUMMARY OF THE INVENTION

The present invention provides a polynucleotide adjuvant composition and methods of use in eliciting an immune response. The present invention also provides an immunogenic composition comprising the polynucleotide adjuvant composition together with an antigen (e.g., as in a vaccine). The adjuvant compositions of the invention have particular physical properties (e.g., molecular weight, size, concentration and pH) which address the need for an effective and safe adjuvant for eliciting an enhanced immune response. The present invention further contemplates methods of use of such adjuvant compositions, particularly in eliciting an immune response to an antigenic compound.

In one embodiment, the invention provides a polynucleotide adjuvant composition comprising polyriboinosinic-polyribocytidylic acid (PIC), an antibiotic and a positive ion, wherein the antibiotic may be kanamycin and the positive ion may be a divalent ion such as calcium. The present invention also provides an immunogenic composition comprising the polynucleotide adjuvant composition together with an antigen or vaccine.

The present invention serves to advance the body of knowledge by defining a novel composition that may be used safely and effectively as an adjuvant to enhance and/or modify the immune response in an animal or human host. While prior disclosures demonstrate the application of the antiviral drug Av-PICKCa for use as an adjuvant, this form of PICKCa was observed to elicit only a limited specific immune response when administered with an antigen. Further PICKCa was found to elicit unacceptable adverse side effects under certain conditions.

The present invention addresses these problems by providing an adjuvant composition, referred to generally herein as "PIKA", which may be administered most effectively and safely as an adjuvant in animals, including humans.

PIKA is a composition comprising a polynucleotide, an antibiotic and a positive ion that has been specifically developed as an adjuvant. Included in the invention are compositions having the unique product attributes that make it most suitable for use as an adjuvant in an immunogenic composition to be administered to animals and/or humans.

More specifically, the present invention provides a polynucleotide adjuvant composition comprising a polynucleotide, an antibiotic and a positive ion, wherein the polynucleotide may be polyriboinosinic-polyribocytidylic acid (PIC); the antibiotic is kanamycin, an anthracycline, butirosin sulfate, a gentamicin, hygromycin, amikacin, dibekacin, nebramycin, metrzamide, neomycin, puromycin, streptomycin or streptozocin; and the ion is calcium, cadmium, lithium, magnesium, cerium, cesium, chromium, cobalt, deuterium, gallium, iodine, iron, or zinc.

More specifically, the present invention provides the specification, including the molecular weight, concentration and pH, of the composition comprising a polynucleotide, an antibiotic and a positive ion that addresses the need for a safe adjuvant which elicits the maximum desired immune response.

The present invention also provides an immunogenic composition comprising the polynucleotide adjuvant composition and an antigen or vaccine.

In certain embodiments the present invention is in the form of a kit comprising the polynucleotide adjuvant and an immunogenic compound.

Furthermore, the present invention provides a method for enhancing immune responses to an antigenic compound by administering to a host the immunogenic composition. The host can be a human being or animal. The administration can be done by injection, such as intramuscular, intraperitoneal, intravenous or subcutaneous injection, or by inhalation. In other embodiments, the immunogenic composition can be delivered rectally, vaginally, nasally, orally, opthamalically, topically, transdermally, or intradermally.

Accordingly, the present invention provides an adjuvant and an immunogenic composition that can be used safely in humans and animals.

Accordingly, in one aspect the invention features a polynucleotide adjuvant composition comprising a polyriboinosinic-polyribocytidylic acid (PIC), an antibiotic, and a positive ion, wherein the composition contains molecules of the adjuvant heterogeneous for molecular weight having a molecular weight of from about 66,000 to 1,200,000 Daltons.

In related embodiments, the polynucleotide adjuvant composition molecules in the composition are heterogeneous for molecular weight, where the molecular weight is from about 300,000 to 1,200,000 Daltons, or from about 66,000 to 660,000 Daltons, or from about 300,000 to 660,000 Daltons, or from about 300,000 to 2,000,000 Daltons, or from about 300,000 to 4,000,000 Daltons, or from about 500,000 to 1,000,000 Daltons, or from about 1,000,000 to 1,500,000 Daltons, or from about 1,500,000 to 2,000,000 Daltons, or from about 2,000,000 to 2,500,000 Daltons, or from about 2,500,000 to 3,000,000 Daltons, or from about 3,000,000 to 3,500,000 Daltons, or from about 3,500,000 to 4,000,000 Daltons, or from about 4,000,000 to 4,500,000 Daltons, or from about 4,500,000 to 5,000,000 Daltons.

In related embodiments, the polynucleotide adjuvant composition molecules in the composition have an average molecular weight equal to or greater than 150,000 Daltons, or equal to or greater than 250,000 Daltons, or equal to or greater than 350,000 Daltons, or equal to or greater than 500,000 Daltons, or equal to or greater than 650,000 Daltons, or equal to or greater than 750,000 Daltons, or equal to or greater than 1,000,000 Daltons, or equal to or greater than 1,200,000 Daltons, or equal to or greater than 1,500,000 Daltons, or equal to or greater than 2,000,000 Daltons.

Accordingly, in one aspect the invention features, a polynucleotide adjuvant composition comprising a polyriboinosinic-polyribocytidylic acid (PIC), an antibiotic, and a positive ion wherein the composition contains molecules of the adjuvant heterogeneous for molecular size having a sediment co-efficient Svedbergs (S) of from about 6.43 S to 24.03 S.

In related embodiments, the polynucleotide adjuvant composition molecules in the composition are heterogeneous for molecular size, where the molecular size is from about 12.8 S to 24.03 S, or from about 6.43 to 18.31 S, or from about 12.8 to 18.31 S, or from about 12.8 S to 30.31 S, or from about 12.8 S to 41.54 S, or from about 13.5 S, to 18.31 S, or from about 13.5 S to 24.03 S, or from about 16.14 to 22.12 S, or from about 22.12 S to 26.6 S, or from about 26.6 S to 30.31 S, or from about 30.31 S to 33.55 S, or from about 33.55 S to 36.45 S, or from about 36.45 S to 39.1 S, or from about 39.1 S to 41.54 S, or from about 41.54 S to 43.83 S, or from about 43.83 S to 45.95 S.

In further related embodiments, the polynucleotide adjuvant composition has an average sedimentation co-efficient (Svedbergs) greater than 9, or greater than 12, or greater than 13.5, or greater than 15, or greater than 16, or greater than 17, or greater than 18, or greater than 19, or greater than 20, or greater than 21, or greater than 22 or greater than 25, or greater than 30.

In a related embodiment the antibiotic in the composition is kanamycin, neomycin, an anthracycline, butirosin sulfate, a gentamicin, hygromycin, amikacin, dibekacin, nebramycin, metrzamide, puromycin, streptomycin or streptozocin.

In a further related embodiment, the adjuvant composition further comprises a source of calcium ions.

In another related embodiment, the positive ion in the composition is calcium, cadmium, lithium, magnesium, cerium, cesium, chromium, cobalt, deuterium, gallium, iodine, iron, or zinc. The positive can be in the form of inorganic salts or organic complexes.

The source of calcium ions can be provided by, for example, calcium chloride, calcium carbonate, calcium fluoride, calcium hydroxide, calcium phosphates, or calcium sulfate.

In one aspect of particular interest, the invention provides a polynucleotide adjuvant composition comprising polyriboinosinic-polyribocytidylic acid (PIC), kanamycin and calcium, wherein the composition includes molecules of the adjuvant heterogeneous for molecular weight having a molecular weight of from about 66,000 to 1,200,000 Daltons. In related embodiments, the polyriboinosinic-polyribocytidylic acid (PIC), kanamycin and calcium molecules have a molecular weight from about 300,000 to 1,200,000 Daltons, or from about 66,000 to 660,000 Daltons, or from about 300,000 to 660,000 Daltons, or from about 300,000 to 2,000,000 Daltons, or from about 300,000 to 4,000,000 Daltons, or from about 500,000 to 1,000,000 Daltons, or from about 1,000,000 to 1,500,000 Daltons, or from about 1,500,000 to 2,000,000 Daltons, or from about 2,000,000 to 2,500,000 Daltons, or from about 2,500,000 to 3,000,000 Daltons, or from about 3,000,000 to 3,500,000 Daltons, or from about 3,500,000 to 4,000,000 Daltons, or from about 4,000,000 to 4,500,000 Daltons, or from about 4,500,000 to 5,000,000 Daltons.

In other related embodiments, the polyriboinosinic-polyribocytidylic acid (PIC), kanamycin and calcium molecules of the adjuvant heterogeneous for molecular weight having an average molecular weight equal to or greater than 150,000 Daltons, equal to or greater than 250,000 Daltons, or equal to or greater than 350,000 Daltons, or equal to or greater than 500,000 Daltons, or equal to or greater than 650,000 Daltons, or equal to or greater than 750,000 Daltons, or equal to or greater than 1,000,000 Daltons, or equal to or greater than 1,200,000 Daltons, or equal to or greater than 1,500,000 Daltons, or equal to or greater than 1,500,000 Daltons.

In one aspect of particular interest, the invention provides a polynucleotide adjuvant composition comprising polyriboinosinic-polyribocytidylic acid (PIC), kanamycin and calcium wherein the composition includes molecules of the adjuvant heterogeneous for molecular size having a sediment co-efficient Svedbergs (S) of from about 6.43 S to 24.03 S.

In related embodiments, the polynucleotide adjuvant composition molecules in the composition are heterogeneous for molecular size, where the molecular size is from about 12.8 S to 24.03 S, or from about 6.43 to 18.31 S, or from about 12.8 to 18.31 S, or from about 12.8 S to 30.31 S, or from about 12.8 S to 41.54 S, or from about 13.5 S to 18.31 S, or from about 13.5 S to 24.03 S, or from about 16.14 to 22.12 S, or from about 22.12 S to 26.6 S, or from about 26.6 S to 30.31 S, or from about 30.31 S to 33.55 S, or from about 33.55 S to 36.45 S, or from about 36.45 S to 39.1 S, or from about 39.1 S to 41.54 S, or from about 41.54 S to 43.83 S, or from about 43.83 S to 45.95 S.

In still other related embodiments, the polyriboinosinic-polyribocytidylic acid (PIC), kanamycin and calcium has an average sedimentation co-efficient greater than 9, or greater than 12, or greater than 13.5, or greater than 15, or greater than 16, or greater than 17, or greater than 18, or greater than 19, or greater than 20, or greater than 21, or greater than 22, or greater than 25, or greater than 30.

In some embodiments the invention provides a polynucleotide adjuvant composition comprising polyriboinosinic-polyribocytidylic acid (PIC), kanamycin and calcium, wherein it may be preferable for the composition to exclude molecules, particularly to an extent that such excluded molecules have no significant immunogenic effect, wherein the excluded molecules have a molecular weight about or below 30,000 Daltons, about or below 40,000 Daltons, about or below 50,000 Daltons, about or below 60,000 Daltons, about or below 70,000 Daltons, about or below 80,000 Daltons, about or below 90,000 Daltons, about or below 100,000 Daltons, about or below 150,000 Daltons, about or below 200,000 Daltons, about or below 250,000 Daltons, about or below 300,000 Daltons, about or below 350,000 Daltons, about or below 400,000 Daltons, about or below 450,000 Daltons, about or below 500,000 Daltons, about or below 600,000 Daltons, about or below 700,000 Daltons, about or below 800,000 Daltons, about or below 900,000 Daltons, about or below 1,000,000 Daltons.

In some embodiments the invention provides a polynucleotide adjuvant composition comprising polyriboinosinic-polyribocytidylic acid (PIC), kanamycin and calcium wherein it may be preferable for the composition to exclude molecules, particularly to an extent that such excluded molecules have no significant immunogenic effect, wherein the excluded molecules have a molecular size about or below 4.49 S, about or below 5.12 S, about or below 5.67 S, about or below 6.16 S, about or below 6.6 S, about or below 7.02 S, about or below 7.4 S, about or below 7.77 S, about or below 9.34 S, about or below 10.64 S, about or below 11.78 S, about or below 12.8 S, about or below 13.73 S, about or below 14.59 S, about or below 15.39 S, about or below 16.14 S, about or below 17.54 S, about or below 18.81 S, about or below 19.99 S, about or below 21.09 S, about or below 22.12 S.

In one aspect of particular interest, the invention provides for an immunogenic composition for enhancing the antigenicity of an antigenic compound comprising the polynucleotide adjuvant composition.

In related embodiments, the immunogenic composition comprises the polynucleotide adjuvant and an antigen.

In related embodiments, the source of the antigen is a human antigen, a non-human animal antigen, a plant antigen, a bacterial antigen, a fungal antigen, a viral antigen, a parasitic antigen, or a cancer antigen.

In related embodiments, the immunogenic composition comprises the polynucleotide adjuvant composition and a rabies antigen.

In certain embodiments, the antigens may be purified from a natural source, synthesized by means of solid phase synthesis, or may be obtained means of recombinant genetics. The antigen may comprise a protein fragment comprising one or more immunogenic regions of the molecule. Antigens can also be provided by whole cells or micro-organisms (e.g. whole viral particles), which may be live, attenuated, or truncated, or killed.

In other embodiments, the antigens include one or more agents from infectious agents, a plant antigen, cancer, allergenic agents and other human antigen such as for developing autoimmune diseases. In other embodiments, the antigens include one or more infectious agents from any of the virus, bacteria, *Mycobacterium*, fungal, and parasites.

The polynucleotide adjuvant composition of the present invention can also be utilized to enhance the immune response against antigens produced by the use of DNA vaccines. The DNA sequences in these vaccines coding for the antigen can be either "naked" or contained in a delivery system, such as liposomes.

In still other related embodiments the rabies antigen is selected from human diploid cells vaccine (HDCV), or hamster kidney cell inactivated purified rabies vaccine (HKC-IPRV), or hamster kidney cell inactivated crude rabies vaccine (HKC-ICRV), or purified vero cell rabies vaccine (PVRV), or purified chicken embryo cell (PCEC), or purified duck embryo vaccine (PDEV), or hamster kidney cell inactivated purified rabies antigen (HKC-IPRA) or hamster kidney cell inactivated crude rabies antigen (HKC-ICRA).

In one aspect of particular interest, the invention provides for an immunogenic composition for enhancing the antigenicity of an antigenic compound comprising the polynucleotide adjuvant composition that is capable of eliciting an antigen specific cell mediated immune response.

In one aspect of particular interest, the invention provides for an immunogenic composition for enhancing the antigenicity of an antigenic compound comprising the polynucleotide adjuvant composition that is capable of eliciting an antigen specific B cell immune response.

In one aspect of particular interest, the invention provides for an immunogenic composition for enhancing the antigenicity of an antigenic compound comprising the polynucleotide adjuvant composition that is capable of eliciting a combined T cell and B cell antigen specific immune response In one aspect of particular interest, the invention provides for an immunogenic composition for enhancing the antigenicity of a compound comprising the polynucleotide adjuvant composition and a hamster kidney cell inactivated purified rabies antigen, where the presence of the rabies antigen should reach a minimum quantity, such as more than 1 International Units (IU).

In related embodiments, the immunogenic composition comprises the polynucleotide adjuvant composition and hamster kidney cell inactivated purified rabies antigen where the presence of the rabies antigen should reach a minimum quantity, such as more than 0.25 International Units, is more than 0.5 International Units, is more than 1.2 International Units, is more than 1.4 International Units, is more than 1.6 International Units, is more than 1.8 International Units, is more than 2.0 International Units, is more than 2.2 International Units, is more than 2.4 International Units, is more than 2.6 International Units, is more than 2.8 International Units, is more than 3.0 International Units, is more than 3.2 International Units, is more than 3.4 International Units, is more than 3.6 International Units, is more than 3.8 International Units, or is more than 4.0 International Units.

In one aspect of particular interest, the invention provides for an immunogenic composition for enhancing the antigenicity of a compound comprising the polynucleotide adjuvant composition and a hamster kidney cell inactivated purified rabies antigen where the presence of the adjuvant and the rabies antigen is in a ratio of about 1 to 1.

In related embodiments, the immunogenic composition comprises the polynucleotide adjuvant composition and a hamster kidney cell inactivated purified rabies antigen where the presence of the adjuvant and the rabies antigen is in a ratio of less than 1 to 10, of about 1 to 9, of about 1 to 8, of about 1 to 7, of about 1 to 5, of about 1 to 4, of about 1 to 3, of about 1 to 2, of about 2 to 1, of about 3 to 1, of about 4 to 1, of about 5 to 1, of about 6 to 1, of about 7 to 1, of about 8 to 1, of about 9 to 1, of about 10 to 1, of greater than 10 to 1.

In one aspect of particular interest, the invention provides for an adjuvant composition or immunogenic composition wherein the immunogenic composition, or the adjuvant composition contained in the immunogenic composition, is in a solid or liquid form or in solution or in suspension.

In one aspect of particular interest, the invention provides for an adjuvant composition or immunogenic composition comprising an adjuvant composition wherein the adjuvant composition or the immunogenic composition is freeze-dried.

In related embodiments the invention provides for a kit comprising the adjuvant composition and an antigenic compound.

In one aspect of particular interest, the invention provides for the use of a polynucleotide adjuvant composition for the preparation of a medicament for enhancing the immunogenic response of a host.

In one aspect of particular interest, the invention provides for a method for enhancing immune responses to an antigenic compound, comprising administering to a host an immunogenic composition for enhancing the antigenicity of an antigenic compound comprising the polynucleotide adjuvant composition.

In related embodiments, the method of administrating to a host the immunogenic composition can be by one way selected from a group including parenteral injection, intramuscular injection, intraperitoneal injection, intravenous injection, subcutaneous injection, inhalation, rectal delivery, vaginal delivery, nasal delivery, oral delivery, opthamalical delivery, topical delivery, transdermal delivery or intradermal delivery.

In one aspect of particular interest, the invention provides for a method for enhancing immune responses to an antigenic compound, comprising administering to a host an immunogenic composition for enhancing the antigenicity of an antigenic compound comprising the polynucleotide adjuvant composition wherein the host is human.

In one aspect of particular interest, the invention provides for a method for enhancing immune responses to an antigenic compound, comprising administering to a host an immunogenic composition for enhancing the antigenicity of an antigenic compound comprising the polynucleotide adjuvant composition wherein the host is an animal.

These and other features and advantages of the invention will become apparent from the following detailed description of preferred embodiments thereof in connection with the accompanying drawings.

DETAILED DESCRIPTION OF EXEMPLARY EMBODIMENTS OF THE INVENTION

The present invention may be understood more readily by reference to the following detailed description of certain embodiments of the invention and the Examples included herein.

Throughout this application, where publications are referenced, the disclosures of these publications are hereby incorporated by reference, in their entireties, into this application in order to more fully describe the state of art to which this invention pertains.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a text" includes a plurality of such texts and reference to "the segment" includes reference to one or more segments and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Definitions of Terms

Prior to setting forth details of the present invention it may be useful to an understanding thereof to set forth definitions of several terms that are used herein.

The term "adjuvant," as used herein, refers to any substance or mixture of substances that increases or diversifies the immune response of a host to an antigenic compound. Specifically:

1. The term "PICKCa" generally refers to a composition of poly I:C, kanamycin and calcium irrespective of particular physical and immunogenic properties.

2. "Av-PICKCa" refers to a form of PICKCa used commercially as an antiviral drug.

3. "PIKA" refers to a composition of the invention comprising poly I:C, an antibiotic (e.g., kanamycin), and a positive ion (e.g., calcium), where the PIKA is characterized by physical characteristics (e.g., molecular weight, size, and the like as described herein) such that upon administration, PIKA exhibits characteristics of an adjuvant with reduced adverse side effects (e.g., reduced toxicity) relative to, for example, PICKCa and greater potency (e.g., stimulates an enhanced immune response) relative to, for example, Av-PICKCa.

"PIC-containing molecule" or "PIC-containing compound" refers to, without limitation, PIC, which may be optionally complexed or otherwise combined with at least one or both of an antibiotic (e.g., kanamycin) and a positive ion (e.g., calcium) present in a composition containing the PIC-containing molecule.

"Heterogeneous" as used herein in the context of the adjuvant compositions of the invention indicates that components of the composition, e.g., the PIC-containing molecules, are not uniform with respect to a physical characteristic of molecular weight, size, or both.

The term "animal" includes humans and all domestic and wild mammals and fowl, including, without limitation, cattle, horses, cows, swine, sheep, goats, dogs, cats, rabbits, deer, mink, chickens, ducks, geese, turkeys, game hens, and the like.

The term "antibody" includes polyclonal and monoclonal antibodies, as well as antigenic compound binding fragments of such antibodies including Fab, F(ab')2, Fd, Fv fragments, and single chain derivatives of the same. In addition, the term "antibody" includes naturally occurring antibodies as well as non-naturally occurring antibodies, including, for example, chimeric, bifunctional and humanized antibodies, and related synthetic isoforms.

As used herein, the term "antigenic compound" refers to any substance that can be recognized by the immune system (e.g., bound by an antibody or processed so as to elicit a cellular immune response) under appropriate conditions.

An "antigen" refers to a substance, including compositions in the form of a vaccine where the vaccine itself comprises an antigenic compound and may or may not comprise an adjuvant other than PIKA, which when administered by an appropriate route (e.g., parenterally), induces an immune response, for example, the formation of antibodies, including antibodies that specifically bind the antigen. Two of the characteristic features of antigens are their immunogenicity, that is, their capacity to induce an immune response in vivo, and their antigenicity, that is their capacity to be selectively recognized by the antibodies whose origins are the antigens.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response normally includes lymphocyte proliferation. When "lymphocyte proliferation" is measured, the ability of lymphocytes to proliferate in response to a specific antigen is measured. Lymphocyte proliferation is meant to refer to B cell, T-helper cell or cytotoxic T-lymphocyte (CTL) cell proliferation.

An "effective amount of an antigenic compound" refers to an amount of antigenic compound which, in optional combination with an adjuvant, will cause the subject to produce a specific immunological response to the antigenic compound.

The expression "enhanced immune response" or similar means that the immune response is elevated, improved or enhanced to the benefit of the host relative to the prior immune response status, for example, before the administration of an immunogenic composition of the invention.

The terms "humoral immunity" and "humoral immune response" refer to the form of immunity in which antibody molecules are produced in response to antigenic stimulation.

The term "immune response" refers to any response to an antigenic compound by the immune system of a vertebrate subject. Exemplary immune responses include, but are not limited to cellular as well as local and systemic humoral immunity, such as CTL responses, including antigen-specific induction of CD8+ CTLs, helper T-cell responses including T-cell proliferative responses and cytokine release, and B-cell responses including antibody response.

The term "eliciting an immune response" is used herein generally to encompass induction and/or potentiation of an immune response.

The term "inducing an immune response" refers to an immune response that is, stimulated, initiated, or induced.

The term "potentiating an immune response" refers to a preexisting immune response that is improved, furthered, supplemented, amplified, enhanced, increased or prolonged.

The term "Poly I:C" or "PIC" refers to a composition containing polyriboinosinic and polyribocytidylic nucleic acids, which may also be referred to as polyinosinic acid-polycytidylic acid, respectively.

The term "immunogenic amount" refers to an amount of antigenic compound sufficient to stimulate an immune response, when administered with the composition of the invention, as compared with the immune response observed in the absence of the polynucleotide adjuvant.

The term "immunopotentiating amount" refers to the amount of the adjuvant needed to effect an increase in antibody titer and/or cell mediated immunity when administered with an antigenic compound in a composition of the invention, as compared with the increase in antibody and/or cell mediated immunity level observed in the absence of the polynucleotide adjuvant.

As used herein, the term "mixing" includes any method to combine the components of the composition; such methods include, but are not limited to, blending, dispensing, dissolving, emulsifying, coagulating, suspending, or otherwise physically combining the components of the composition.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The term "treatment" covers any treatment of a disease in a vertebrate animal, particularly a human, and includes: (i) preventing the disease from occurring in a subject which may be predisposed to the disease but has not yet been diagnosed as having it; (ii) inhibiting the disease, i.e., arresting its development; or (iii) relieving the disease, i.e., causing regression of the disease.

The term "unit dosage form" as used herein refers to physically discrete units suitable as unitary dosages for human and animal subjects, each unit containing a predetermined quantity of compounds of the present invention calculated in an amount sufficient to produce the desired effect in association with a pharmaceutically/physiologically acceptable diluent, carrier or vehicle.

Overview of the Invention

The present invention is directed to compounds and methods useful for the enhancement of an immune response, which may be humoral and/or cell-mediated, in a human, animal or cell culture. In general the composition comprises of an immunogenic composition containing an adjuvant. The presence of the adjuvant enhances or modifies the immune response. Thus, the humoral and/or cell-mediated immune responses are more effective with the presence of the adjuvant. Furthermore, the adjuvant may alter the quality of the immune response by affecting the subclasses (isotypes) of immunoglobulins and cytokines produced.

The key characteristics of the adjuvant are its ability to stimulate a desired level and type of immune response without inducing adverse side effects. There are currently only a limited number of adjuvants approved for human use that have such a combination of characteristics. The safety standards for immunogenic substances and particularly vaccines are strict and rigorously enforced. Therefore, a significant constraint for the development of a successful adjuvant is the development of a product that is sufficiently potent so as to elicit an appropriate immune response while not inducing adverse side effects.

The preferred embodiment of the invention is a polynucleotide adjuvant wherein the polynucleotide is polyriboinosinic-polyribocytidylic acid (PIC). PIC alone has shown to be an effective adjuvant but exhibits an unacceptable safety profile and is unstable in human and primates. The current invention provides a composition of PIC combined with an antibiotic and positive ion that enhances the desired immunogenic attributes of an adjuvant while improving the safety and stability profile.

The present invention is further based on the discovery that the physical and biological characteristics of the PIKA molecules of the adjuvant composition influence the characteristics of the immune response and adverse side effects. In the course of investigative research studies it was unexpectedly discovered that by adjusting certain characteristics of the polynucleotide adjuvant it becomes more or less potent and/or more or less toxic in ways that are further described below. Therefore by defining the composition of the adjuvant in terms of its physical characteristics it is possible to describe more precisely the attributes of the adjuvant composition that provides a preferable immunogenic response and preferable safety/stability profile.

The adjuvant of the current invention, referred to herein for convenience as the PIKA adjuvant, is therefore fully defined by a combination of its chemical composition plus the fundamental physical attributes of the molecules that make up the adjuvant. Thus the particular form of PIKA that exhibits significantly superior immunogenic properties while being safe to use in animals and humans is best defined by one or more, usually a combination of, specific attributes including; composition, molecular weight, molecular size, concentration, and pH.

PIKA generally comprises a polynucleotide, an antibiotic, and a positive ion, where the polynucleotide may be polyriboinosinic-polyribocytidylic acid (PIC), and the antibiotic an aminoglycoside (e.g., kanamycin, streptomycin, tobramycin), neomycin, an anthracycline, butirosin sulfate, a gentamicin, hygromycin, amikacin, dibekacin, nebramycin, metrzamide, puromycin, or streptozocin, and the ion is calcium, cadmium, lithium, magnesium, cerium, cesium, chromium, cobalt, deuterium, gallium, iodine, iron, or zinc.

The "aminoglycoside" antibiotics refer to antibiotics whose structure contains amino sugars attached to an, aminocyclitol ring (hexose nucleus) by glycosidic bonds. Aminoglycoside antibiotics are derived from various species of *Streptomyces* and *Micromonospora* or are produced synthetically. For example, kanamycin is an aminoglycoside antibiotic obtained from the soil bacterium *Steptomyces Kanamycetics*, used in the treatment of various infections, especially those caused by Gram-negative bacteria.

The PIKA composition is manufactured through the mixing of polyinosinic acid, polycytidylic acid, an antibiotic and the source of a positive ion in a sodium chloride/phosphate buffer solution that has a pH between pH 6 and pH 8. The polyinosinic acid and polycytidylic acid are generally provided at a concentration of 0.1 to 10 mg/ml, preferably 0.5 to 5 mg/ml and more preferably 0.5 to 2.5 mg/ml. The hyperchromicity value should be greater than 10%, preferably greater than 15% and more preferably greater than 20%. The preparation of the PIC and the combination with the kanamycin and calcium is preferably conducted under quality standards consistent with international Good Manufacturing Process.

In certain embodiments of the present invention, the kanamycin in the polynucleotide adjuvant composition may be used together with or substituted by one or more antibiotics selected from the group including tobramycin, anthracyclines, butirosin sulfate, gentamicins, hygromycin, amikacin, dibekacin, nebramycin, metrzamide, neomycin, puromycin, streptomycin and streptozocin. The antibiotic (e.g., Kanamycin or the like) in the polynucleotide adjuvant composition of the invention is generally provided at a concentration of from about 10 to 100,000 units/ml, preferably from about 100 to 10,000 units/ml, and more preferably from about 500 to 5,000 units/ml.

In certain embodiments of the present invention, the polynucleotide adjuvant composition further comprises a positive ion (cation), usually a divalent cation, normally a cation of an alkali metal. The positive ion is generally provided in the composition of the invention as a source of positive ions such as a salt or complex, e.g., an organic or inorganic salt or complex, usually an inorganic salt or organic complex. Exemplary positive ions include, but are not necessarily limited to, calcium, cadmium, lithium, magnesium, cerium, cesium, chromium, cobalt, deuterium, gallium, iodine, iron, or zinc.

The positive ion (e.g. calcium) can be provided in the composition of the invention at a concentration in the range of from about 10 umol to 10 mmol/ml, preferably from about 50 umol to 5 mmol/ml, and more preferably from about 100 umol to 1 mmol/ml.

As noted above, the positive ion can be provided in the form of any suitable salt or organic complex, including, but not necessarily limited to chloride, fluoride, hydroxide, phosphate, or sulfate salts. For example, where the positive ion is calcium, the ion can be in the form of calcium carbonate, calcium chloride, calcium fluoride, calcium hydroxide, calcium phosphates, or calcium sulfate.

Where the positive ion in the adjuvant composition of the invention is calcium, it can be in combination with or substituted by other positive ions, including cadmium, lithium, magnesium, cerium, cesium, chromium, cobalt, deuterium, gallium, iodine, iron, and zinc, wherein the ions can be in the form of inorganic salts or organic complexes.

The resulting composition is further transformed into PIKA through an additional manufacturing process that involves the isolation of molecules of a defined molecular size and/or weight. The separation of polynucleotide molecules of particular characteristics using filtration, chromatography, thermal treatment, centrifugal separation, electrophoresis, and similar methods that are standard processes are known to those skilled in the art.

In certain embodiments of the present invention, the polynucleotide adjuvant composition is further defined by the physical attribute of molecular weight. In the course of investigation it was surprisingly found that there is a positive correlation between molecular weight and the efficacy of the polynucleotide adjuvant composition. The observed level of potency of an immunogenic composition containing the polynucleotide adjuvant composition, including the ability to elicit the production of immunoglobulins and cytokines, increases as the molecular weight of the polynucleotide adjuvant composition increases. The molecular weight of the polynucleotide adjuvant can be determined by argarose gel electrophoresis as described in Example 1.

As illustrated in the Examples section below, the inventor has discovered that vaccine compositions containing a PIKA adjuvant of a variety of molecular weights exhibited a direct correlation between molecular weight and antigen specific protective potency (see Example 2). Likewise, the inventor has discovered that there is a direct correlation between the molecular weight of PIKA adjuvant compositions and the ability to elicit the production of interferon-gamma when administered to a host in combination with a rabies antigen (see Example 3).

The inventor further identified, during human trials in 1996 in China using a rabies vaccine with an adjuvant comprising PICKCa of a particularly high molecular weight specification, that the resulting composition was surprisingly shown to have an unacceptable level of adverse side effects. The results from the clinical trial in 1996 that have not previously been published are presented in Example 4. The research into the molecular weight is presented in Examples 5 and 6. The trial was conducted under the jurisdiction of the Chinese Food and Drug Administration. Thus the adjuvant would not have been administered to humans in a controlled clinical trial environment if such side effects had been anticipated based on the knowledge at that time.

The inventor has found that PIKA adjuvant compositions of the invention in pre-clinical studies with molecular weights up to $1.0 \times 10^6$ and compositions of vaccines including PIKA adjuvant compositions with molecular weights of up to $5.5 \times 10^5$ have demonstrated a wide safety margin in specific toxicity tests (see Example 7). PIKA with a maximum molecular weight of $1.2 \times 10^6$ has been successfully used in pre-clinical research (see Example 3). Further research conducted by the inventor demonstrates the safety of PIKA when used in conjunction with an antigen compound in the form of a vaccine (see Example 8).

Results from a subsequent experiment conducted by the inventor in China in 2002 also demonstrate that the use of PIKA provides a safe and effective adjuvant in humans. The results of this experiment, not previously published, are presented in Example 9.

Based on the above observations, the preferred embodiment of PIKA therefore comprises molecules having physical characteristics of molecular weight and/or size that provide benefit from the increase in potency and efficacy while providing an adequate degree of safety margin so as not to induce any adverse side effects. Molecules present in Av-PICKCa, at the lower end of the molecular weight range, may be effective as an antiviral composition but are significantly less effective than the molecular composition of PIKA when used as an adjuvant in an immunogenic composition. Further, PIKA has been shown to have a safety profile that is preferable to PICKCa.

One aspect of the current invention is thus the molecular weight of PIKA, the composition of the invention.

The inventive composition of PIKA generally comprises a collection or population of molecules, where the molecules have physical characteristics of, for example, molecular weight and/or size, that provide for a desired effect in eliciting an immune response while, preferably, mitigating or avoiding adverse side effects (such as those associated with the administration of PICKCa). Generally, the molecules of PIKA are heterogeneous for molecular weight and/or size.

As generally used herein and unless specifically indicated otherwise, PIKA, the adjuvant composition of the invention, includes PIC which may be complexed with an antibiotic (e.g., kanamycin) and a positive ion (e.g., calcium). The molecules in PIKA are heterogeneous in molecular weight (e.g., as assessed by Daltons) or size (e.g., as assessed by sedimentation coefficient).

Where a range is used in reference to a heterogeneous characteristic of PIKA molecules (e.g., molecular weight or size), reference to such a range herein indicates the approximate lower and upper limits of the molecular weights or sizes of the PIKA molecules in the composition, but does not imply or intend that the composition contains a PIKA molecule that has a molecular weight or size that is representative of every molecular weight or size within the range. Thus, for example, a molecular weight range of from about 66,000 to 1,200,000 Daltons indicates that PIKA molecules of about 66,000 Daltons and about 1,200,000 Daltons are contained in the composition, but there is no requirement that PIKA molecules of 88,000 Daltons be present in the composition (although, indeed, such may be present).

Where a physical characteristic of the PIKA molecules in the inventive composition is defined by a range of molecular weights, the PIKA molecules are heterogeneous for molecular weight, wherein the molecular weight range is from about 300,000 to 660,000 Daltons, from about 300,000 to 1,200,000 Daltons, from about 66,000 to 660,000 Daltons, or from about 66,000 to 1,200,000 Daltons.

The invention also contemplates compositions having PIKA molecules heterogeneous for molecular weight, where the molecular weight range is from about 300,000 to 2,000,000 Daltons, from about 300,000 to 4,000,000 Daltons, from about 500,000 to 1,000,000 Daltons, from about 1,000,000 to 1,500,000 Daltons, from about 1,500,000 to 2,000,000 Daltons, from about 2,000,000 to 2,500,000 Daltons, from about 2,500,000 to 3,000,000 Daltons, from about 3,000,000 to 3,500,000 Daltons, from about 3,500,000 to 4,000,000 Daltons, from about 4,000,000 to 4,500,000 Daltons, or from about 4,500,000 to 5,000,000 Daltons. PIKA molecules having molecular weights at the upper and lower limits of these ranges, as well as within these ranges, are present in the composition.

Where a physical characteristic of the PIKA molecules in the inventive composition is defined by average molecular weight, the PIKA molecules can have an average molecular weight equal to or greater than 150,000 Daltons, equal to or greater than 250,000 Daltons, equal to or greater than 350,000 Daltons, equal to or greater than 500,000 Daltons, equal to or greater than 650,000 Daltons, equal to or greater than 750,000 Daltons, equal to or greater than 1,000,000 Daltons, equal to or greater than 1,200,000 Daltons, equal to or greater than 1,500,000 Daltons, or equal to or greater than 2,000,000 Daltons.

Where a physical characteristic of the PIKA molecules in the inventive composition is defined by a sedimentation coefficient, which is a measure of molecular weight and size, the PIKA molecules can have a sedimentation co-efficient greater than 9, or greater than about 12, or greater than about 13.5, or greater than 15, or greater than 16, or greater than 17, or greater than 18, or greater than 19, or greater than 20, or greater than 21, or greater than 22, or greater than 25, or greater than 30.

In some embodiments, the invention provides a polynucleotide adjuvant composition comprising polyriboinosinic-polyribocytidylic acid (PIC), kanamycin and calcium wherein the composition excludes a detectable amount of molecules which have a molecular weight about or below 30,000 Daltons, about or below 40,000 Daltons, about or below 50,000 Daltons, about or below 60,000 Daltons, about or below 70,000 Daltons, about or below 80,000 Daltons, about or below 90,000 Daltons, about or below 100,000 Daltons, about or below 150,000 Daltons, about or below 200,000 Daltons, about or below 250,000 Daltons, about or below 300,000 Daltons, about or below 350,000 Daltons, about or below 400,000 Daltons, about or below 450,000 Daltons, about or below 500,000 Daltons, about or below 600,000 Daltons, about or below 700,000 Daltons, about or below 800,000 Daltons, about or below 900,000 Daltons, or about or below 1,000,000 Daltons. In this embodiment, exclusion of such lower molecular weight molecules is particularly of interest to an extent that such excluded molecules have no significant immunogenic effect.

PIKA comprising molecules of a molecular weight of up to $1.0 \times 10^6$ Daltons has been shown by the inventor to be safe in animals in specific toxicity tests (see Example 7). PIKA comprising molecules of a molecular weight of up to $1.2 \times 10^6$ Daltons has been safely used in pre-clinical studies (see Example 3). PIKA has also been shown to be safe when used in a immunogenic composition (see Example 8). Such a composition of PIKA provides benefits in terms of effectiveness. PIKA comprising molecules of a molecular weight up to $6.6 \times 10^5$ Daltons also elicits an effective immune response with a wider margin of safety when used in humans and animals. Raising the molecular weight of the smallest molecules present to $6.6 \times 10^5$ Daltons and preferably to $3.0 \times 10^5$ Daltons improves the effectiveness of the adjuvant without compromising safety standards.

It has been further discovered that the concentration of the polynucleotide adjuvant composition may impact the molecular weight of the molecules contained in the composition. The molecular weight of PICKCa has been shown to increase as concentration of the adjuvant composition (see Example 5) increases. The inventor has observed that increasing concentration of the polynucleotide adjuvant may result in the coalescence (or aggregation) of the PICKCa molecules, resulting in molecules with a large molecular weight. This process has been shown to be irreversible. Thus the subsequent dilution of the polynucleotide adjuvant composition in a suitable medium does not result in a reduction in molecular weight of the adjuvant molecules. As observed in Example 6, when the concentrated large molecular form of polynucleotide adjuvant composition is combined with the rabies antigen, the result is a composition that retains its high molecular weight range. A rabies vaccine formed in this way demonstrated adverse side effects in human clinical trials (see Example 4).

The PIKA composition of the invention can be provided in any physiologically acceptable buffer may be used herein, but phosphate buffers are preferred. Other acceptable buffers such as acetate, tris, bicarbonate, carbonate, or the like may be used as substitutes for phosphate buffers.

The pH of the aqueous component will preferably be between 4.0 and 10.0 though it is preferable to adjust the pH of the system from 6 to 8.5 where that pH does not significantly reduce the stability of other composition components and is not otherwise physiologically unsuitable. In certain embodiments the aqueous portion of the immunogenic composition is buffered saline. When these compositions are intended for parenteral administration, it is preferable to make these solutions so that the tonicity, i.e., osmolality, is essentially the same as normal physiological fluids in order to prevent post-administration swelling or rapid absorption of the composition because of differential ion concentrations between the composition and physiological fluids.

The quantity of buffered saline employed in these compositions will be that amount necessary to bring the value of the composition to unity. That is, a quantity of buffered saline sufficient to make 100% will be mixed with other components in order to bring the composition to volume.

In certain embodiments, the antigens may be purified from a natural source, synthesized by means of solid phase synthesis, or may be obtained by means of recombinant genetics. The antigen may comprise a protein fragment comprising one or more immunogenic regions of the molecule. Antigens can also be provided by whole cells or micro-organisms (e.g., whole viral particles), which may be live, attenuated, truncated, or killed.

In other embodiments, the antigens include one or more agents from infectious agents, a plant antigen, cancer, allergenic agents and other human antigen, such as for developing autoimmune diseases. In other embodiments, the antigens include one or more infectious agents from any of the virus, bacteria, *Mycobacterium*, fungal and parasites.

The polynucleotide adjuvant composition of the present invention can also be utilized to enhance the immune response against antigens produced by the use of DNA vaccines. The DNA sequences in these vaccines coding for the antigen can be either "naked" or contained in a delivery system, such as liposomes.

In certain embodiments, the polynucleotide adjuvant composition can be used in combination with vaccines. It does not matter whether the vaccine contains adjuvants or not. Vaccines classes included are anti-infectious diseases, anti cancer, anti-allergy, anti-autoimmune diseases, and immunocontraception.

The invention also contemplates use of the polynucleotide adjuvant of the invention in combination with any suitable rabies antigen.

In certain embodiments, the rabies antigen can be an inactivated crude rabies antigen such as a hamster kidney cell inactivated crude rabies antigen (HKC-ICRA) or an inactivated purified rabies antigen such as a hamster kidney cell inactivated purified rabies antigen (HKC-IPRA).

In certain embodiments, the polynucleotide adjuvant composition can be used with a rabies vaccine. Suitable rabies vaccines are commercially available or in research development including inactivated, subunit, recombinant and peptide vaccines such as human diploid cells vaccine (HDCV), or hamster kidney cell inactivated purified rabies vaccine (HKC-IPRV), or hamster kidney cell inactivated crude rabies vaccine (HKC-ICRV), or purified vero cell rabies vaccine (PVRV), or purified chicken embryo cell (PCEC), or purified duck embryo vaccine (PDEV). However, not all of the rabies vaccines elicit a cell-mediated immune response which is important in pre- and post-exposure immunizations. When the polynucleotide adjuvant composition (e.g., PIKA) is administered with the rabies vaccine, the immune responses induced include; non-specific responses (e.g., increased functions of macrophages), humoral responses (e.g., increased specific antibody production), and cell-mediated responses (e.g., production of cytokines including interferon and interleukin-2).

In certain embodiments, the invention provides for a kit comprising the polynucleotide adjuvant and an antigenic compound.

An immunogenic composition including PIKA is able to induce a specific immune response in two ways: i) humoral-mediated immunity, which includes B cell stimulation and production of antibodies or immunoglobulins (other cells are also involved in the generation of an antibody response, e.g. antigen-presenting cells (APCs, including macrophages), and helper T cells (Th1 and Th2)), and ii) cell-mediated immunity, which generally involves T cells including cytotoxic T lymphocytes (CTLs), although other cells are also involved in the generation of a CTL response (e.g., Th1 and/or Th2 cells and APCs). Methods for assessing humoral and/or cellular immune response in an individual are well known in the art. (see Examples 10, 11, 12 and 13).

Furthermore, the polynucleotide adjuvant composition may alter the quality of the immune response by affecting the subclasses (isotypes) of immunoglobulins produced (IgG1, IgG2, IgG3, and IgG4 for human IgGs; IgG1, IgG2a, IgG2b, and IgG3 for mouse IgGs), as well as their affinities.

A response regulated by Th1 cells in mice will induce IgG1, IgG2a, IgG2b and to a lesser extent IgG3, and also will favor a cell mediated immune response to an antigen. If the IgG response to an antigen is regulated by Th2 type cells, it will predominantly enhance the production of IgGI and IgA.

NIH potency tests using a composition of the PIKA adjuvant and a hamster kidney cell inactivated purified rabies antigen surprisingly showed that immunogenic potency of the composition requires a minimum presence of rabies antigen (see Example 14). The potency of the composition increases rapidly relative to the presence of additional rabies antigen in excess of 1 IU of antigen. Thus the rate of increase in potency of the composition was observed to be greatest with around 1.5 IU to 2.5 IU of the rabies antigen present in the composition. The NIH potency test is described in: Laboratory Techniques in Rabies, Edited by F X Meslin, M M Kaplan H Koprowski, 4th Edition, ISBN 92 4 1544 1.

Tests using a composition of the PIKA adjuvant and a hamster kidney cell inactivated purified rabies antigen demonstrated that the immunogenic potency of the composition increased as the quantity of adjuvant present exceeded the amount of antigen present. The potency increased when the ratio of PIKA to hamster kidney cell inactivated purified rabies antigen was increased with the preferred ratio being greater than 3:1. (see Example 15).

The invention contemplates methods of use of the polynucleotide adjuvant of the invention with an antigen to, for example, elicit an antigen specific humoral response and/or specific cellular (e.g., T cell) response in a subject. The immune response elicited may be a response to an antigen in a naïve subject, or may serve to enhance an existing immune response (e.g., as in a booster).

In certain embodiments, the PIKA adjuvant composition and an immunogenic composition comprising the PIKA adjuvant and antigenic compound may be freeze-dried (lyophilized) for long term stability and storage in a solid form. The freeze-dried method is known to those skilled in the art. The reconstitution of the immunogenic composition containing PIKA and an antigenic compound demonstrated a sustained level of effectiveness (see Example 16).

The immunogenic composition may be prepared as an injectable, liquid solution, suspension or emulsion. The preparation of formulations of a desired immunogenic composition is generally described in New Trends and Developments in Vaccines, edited by Voller et al., University Park Press, Baltimore, Md., USA, 1978. The immunogenic composition of the present invention may be employed in such forms as capsules, liquid solutions, emulsions, suspensions, or elixirs for oral administration, or sterile liquid forms such as solutions, emulsions, or suspensions. Any inert carrier is preferably used, such as saline, or phosphate buffered saline, or any such carrier in which the compounds used in the method of the present invention have suitable solubility properties for use in the methods of the present invention.

The immunogenic composition of the present invention can be administered to a subject using a variety of methods known in the art. In certain embodiments, the immunogenic composition can be delivered parenterally, by injection, such as intramuscular, intraperitoneal, intravenous, or subcutaneous injection, or by inhalation. In other embodiments, the immunogenic composition can be delivered rectally, vaginally, nasally, orally, opthamalically, topically, transdermally or intradermally. When the mode of administration is by injection, the encapsulated antigenic compound may stay at the injection site for up to two weeks, thus providing a depot of antigen that will give sustained release or pulsatile release in vivo. Such a delivery system may allow single shot immunogenic formulations to be produced for antigenic compounds that would otherwise require multiple injections to elicit an immune response.

For parenteral administration in an aqueous solution, for example, the solution should be suitably buffered if necessary and the liquid diluent first rendered isotonic with sufficient saline or glucose. These particular aqueous solutions are especially suitable for intravenous and intraperitoneal administration. In this connection, sterile aqueous media which can be employed will be known to those of skill in the art in light of the present disclosure. Exemplary injection media which can be used in the present invention include a buffer with or without dispersing agents and/or preservatives, and edible oil, mineral oil, cod liver oil, squalene, mono-, di- or triglyceride, and a mixture thereof.

The exact amount of such compositions required will vary from subject to subject, depending on the species, age, weight, and general conditions of the subject, the severity of the disease, infection, or condition that is being treated or prevented, the particular compound used, its mode administration, and the like. An appropriate amount may be determined by one of ordinary skill in the art using only routine experimentation given the teachings herein. Following an initial administration, subjects may receive one or several booster immunizations adequately spaced.

The above disclosure generally describes the present invention. The following examples will be of assistance to the understanding of the present invention. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Determination of the Molecular Weight of PIKA and Av-PICKCa

This example illustrates how the molecular weight was determined for the PIKA adjuvant in comparison with Av-PICKCa.

Figure 1:
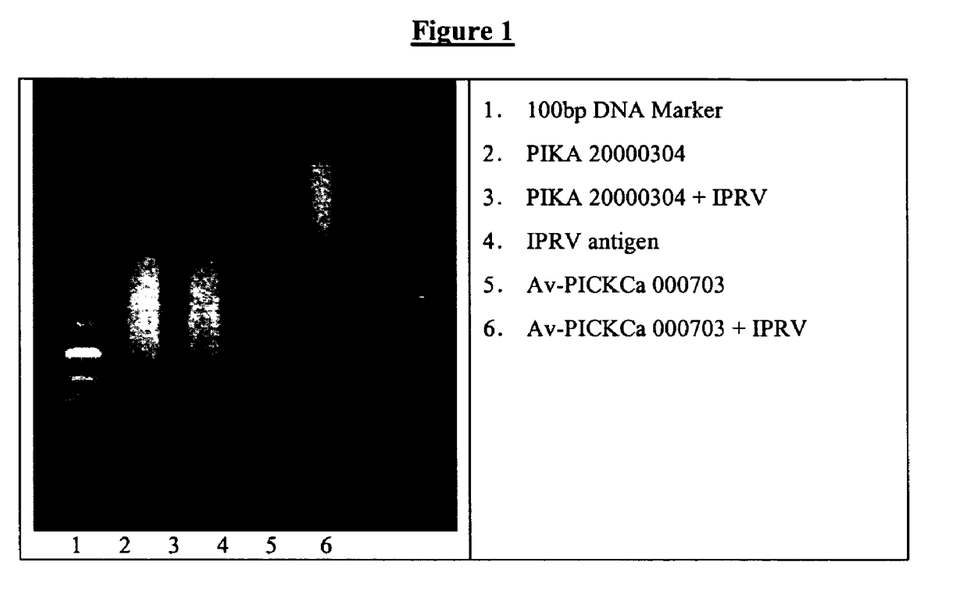
FIG. 1 shows the relative molecular weight for samples of Av-PICKCa and PIKA

Argarose gel electrophoresis is known to those skilled in the art, so that only the particulars to this invention are described herein. The argarose gel used in the present invention had a concentration of 1.5% argarose. The molecular markers were 100 bp DNA ladders from 100 bp to 1000 bp corresponding to a range of molecular weight from $6.6 \times 10^4$ to $6.6 \times 10^5$ Daltons. The loading samples were 4 ul at 1 mg/ml. FIG. 1 shows a representative picture of the result of the samples on the argarose gel following the teachings of this paragraph. The five (5) different batches tested showed a wide range of distribution of their molecular weights. The upper limits of their molecular weights ranged from $2.3 \times 10^5$ Daltons for Av-PICKCa to $5.28 \times 10^5$ Daltons for PIKA.

Example 2

Immune Efficacy of PIKA Compared with Av-PICKCa

This example demonstrates the difference between the potency of Av-PICKCa with a maximum molecular weight of 230,000 Daltons and samples of PIKA with a maximum molecular weight of up to 528,000 Daltons.

Three batches of the PIKA adjuvant of different molecular weight and one batch with molecules of molecular the weight corresponding to that of Av-PIKA were combined with the hamster kidney cell inactivated purified rabies antigen (HKC-IPRA). The, resulting compositions were subjected to the NIH efficacy test.

The NIH test is a rigorous and extensive comparative study between the rabies vaccine under investigation and a standardized rabies vaccine. The vaccinated mice are infected with a strain of live rabies virus and their survival rate is measured. The different groups of mice are administered with different dilutions of the rabies vaccine. A comparison of the survival rates between the groups of mice exposed to the experimental and standardized vaccine determines the potency of the experimental vaccine (Laboratory Techniques in Rabies, Edited by F X Meslin, M M Kaplan H Koprowski, $4^{th}$ Edition, ISBN 92 4 1544 1).

The efficacy of each combined vaccine has been normalized in relation to the standard, non-combined vaccine, where the efficacy of the non-combined one was designated as 1, and the relative efficacy was designated as the times by which the efficacy of a combined one had increased over the non-combined one. Table 1 summarizes the results. As seen from Table 1, the higher the molecular weight of the PICKCa adjuvant, the higher the efficacy of increasing the titer of rabies vaccine.

TABLE 1

Effects of the Molecular Weight on Rabies Vaccine Potency

| Adjuvant Type | Antigen | Sample # | Adjuvant's Upper Limit of Molecular Weight | $ED_{50}$ | Potency (IU/ml) |
|---|---|---|---|---|---|
| PIKA | HKC-IPRA | 20000304 | $5.28 \times 10^5$ | 2.10 | 5.00 |
| PIKA | HKC-IPRA | 20000907 | $4.62 \times 10^5$ | 2.00 | 3.98 |
| PIKA | HKC-IPRA | 990202 | $3.96 \times 10^5$ | 1.98 | 3.80 |
| Av-PICKCa | HKC-IPRA | 000703 | $2.30 \times 10^5$ | 1.88 | 3.00 |
|  | HKC-IPRA | Vaccine control |  | 1.40 | 1.00 |

Example 3

Interferon Production Comparison Between PIKA and Av-PICKCa

This example demonstrates the difference in ability to elicit the production of interferon between samples of Av-PICKCa with a maximum molecular weight of 230,000 Daltons and samples of PIKA with a maximum molecular weight of up to 1,200,000 Daltons.

Two batches of PIKA with upper limits of molecular weight of $1.2 \times 10^6$ Daltons and $4.6 \times 10^5$ Daltons were compared with a batch of Av-PICKCa with an upper limit of molecular weight of $2.3 \times 10^5$ Daltons.

Compositions of the PIKA and Av-PICKCa were combined with hamster kidney cell inactivated purified rabies antigen (HKC-IRPA). The compositions were injected subcutaneously into mice. After two hours, the interferon presence in each mouse was determined. The general procedure for the interferon measurement is known to those in the art. Briefly, in a 96-well plate, each well was inoculated with L929 cells at 0.15 ml/well with about 30,000 cells. After three (3) days when the cells grew to confluence, wells were added into sera samples (0.1 ml/well) wherein the sera were diluted by 1:20 to 1:640. Three wells were for each diluted sample. The wells were incubated overnight at 37° C. The sera samples were washed away. Vesicular stomatitis virus VSV particles were used to detect the interferon production. Table 2 shows the interferon production induced by the mixtures. As seen from Table 2, the higher the molecular weight of the PIKA samples, the better the interferon production induced.

TABLE 2

The Relationship Between Molecular Weight and Interferon Production

| Adjuvant Type | Batch # | Upper Range of Molecular Weight Daltons | HKC-IPRA Batch # | PIKA: HKC-IPRA Ratio | Titer of Interferon Production |
|---|---|---|---|---|---|
| PIKA | 20010601 | $1.20 \times 10^6$ | 20001205 | 4:1 | 868.6 |
| PIKA | 200009-7 | $4.62 \times 10^5$ | 20001205 | 4:1 | 530.6 |
| Av-PICKCa | 000703 | $2.30 \times 10^5$ | 20001205 | 4:1 | 46.4 |

Example 4

1996 Human Vaccine Clinical Trial (with Toxic Side Effects)

This example demonstrates that the PICKCa adjuvant when combined with a vaccine generates an unacceptable level of side effects when administered for human use.

The objective of the study was to evaluate the safety and immune response of a rabies vaccine comprising PICKCa adjuvant at a concentration of 11.95 mg/ml and molar mass of 69,700 (note molar mass is not equivalent to Daltons in this case, see Example 5) and a hamster kidney cell inactivated crude rabies antigen (HKC-ICRA). The results and conclusions from the above clinical trial have not previously been released into the public domain.

The 40 patients participating in the trial were divided into two groups of 20 people. Each group received five (5) doses of 2 ml administered intramuscularly on day 1, day 3, day 7 and day 30. One group received the rabies antigen with the PICKCa adjuvant and the other group received the rabies antigen with an alum adjuvant.

From a safety perspective, observations were made of body temperature, local, and systemic symptoms at 24 hours, 48 hours and 72 hours after each injection. The following observations were:

TABLE 3

Adverse effects after injection of HKC-ICRA with Alum or PICKCa

| Side Effect | Group | Number of Volunteers | Number with Adverse effect |
|---|---|---|---|
| Local | PICKCa plus HKC-ICRA | 20 | 6 |
|  | Alum plus HKC-ICRAx5 | 20 | 2 |
| Systemic | PICKCa plus HKC-ICRA | 20 | 4 |
|  | Alum plus HKC-ICRAx5 | 20 | 0 |

Systemic adverse effects included: fever (1), rash (2), joint pain (2), lymph node (1), throat edema (1). Local Adverse effects included: red skin at injection site (6)

Subsequent research by the inventor attributed the side effects observed to the molecular size of the molecules in the adjuvant (see Examples 5 and 6).

Example 5

Relationship Between PICKCa Concentration and Its Molecular Weight

This example demonstrates that increasing the concentration of the PICKCa adjuvant results in a composition with an increased molecular weight.

PICKCa can be made in different concentrations. It was hypothesized that the PICKCa as a complex of polymers would exist in different forms when it was prepared in different concentrations. Laser light scattering was used for this purpose. Laser light scattering has been broadly used to determine weight-average molar mass (Mw) and radius of gyration (Rg). The instruments are commercially available and the process is known to those skilled in the art. Table 4 shows that the observed molecular weight of PICKCa by laser light scattering correlated to its concentration.

TABLE 4

The Observed Molecular Weight by Laser Light Scattering

| Concentration of PICKCa (mg/ml) | Weight-average Molar Mass |
|---|---|
| 11.95 | $6.97 \times 10^4$ |
| 2.00 | $7.30 \times 10^3$ |
| 1.00 | $2.00 \times 10^3$ |

Example 6

Relationship Between Pre-Concentration of PICKCa and Molecular Weight of Vaccine This example demonstrates a correlation between the increased molecular weight of the PICKCa adjuvant and the resulting molecular weight of the composition that includes the PICKCa adjuvant and a hamster kidney cell inactivated crude rabies antigen.

It was also suspected that the pre-combination concentration of PICKCa samples would affect the antigens in vaccines. Samples of PICKCa were combined with a hamster kidney cell inactivated crude rabies antigen. Laser light scattering was used for this purpose. Laser light scattering has been broadly used to determine weight-average molar mass (Mw) and radius of gyration (Rg). The instruments are commercially available and the process is known to those skilled in the art. Table 5 shows that an increase of pre-combination concentrations of PICKCa resulted in an increase of the Mw of rabies vaccines.

TABLE 5

Relationship Between Pre-combination Concentration of PICKCa and the Mw of Rabies Vaccines

| Concentration of PICKCa (mg/ml) | Weight-average Molar Mass | Radius of Gyration |
|---|---|---|
| 11.95 | $29.6 \times 10^4$ | $17.2 \times 10^2$ |
| 4.00 | $22.2 \times 10^4$ | $15.0 \times 10^2$ |
| 2.00 | $13.8 \times 10^4$ | $11.8 \times 10^2$ |
| 1.00 | $5.60 \times 10^4$ | $7.55 \times 10^2$ |
| 1.00 | $5.29 \times 10^4$ | $6.50 \times 10^2$ |

Example 7

PIKA Toxicity Test

This example demonstrates the safety characteristic of the PIKA adjuvant when there is a restriction on the maximum molecular weight.

A toxicity test was conducted in accordance with the provisions of China National Drug Standard (WS1-XG-050-2000). Briefly, five (5) mice with a body weight of about 18-22 grams are injected intravenously with 0.5 ml/mouse of a sodium chloride solution containing 0.3 mg of a PIKA adjuvant having an upper molecular weight from about 525,000 to about 1,000,000 Daltons. The injected mice are observed for 7 days and weighed at the end of the observation. Table 6 summarizes the results that showed that the molecular weight of the PIKA adjuvant could be as high as $1.0 \times 10^6$ Daltons without obvious toxicity.

TABLE 6

PIKA Adjuvant Toxicity Test

| Batch # | Upper Range of Molecular Weight (Daltons) | Pre-test bodyweight of mice (g) | Amount of tail vein injection | Status of mice at the end of test | Post-test body weight of mice | Remarks |
|---|---|---|---|---|---|---|
| 20000304 | $5.25 \times 10^5$ | 18-19 | 0.5 ml/mouse | Healthy | 23-26 | Satisfactory |
| 20010103 | $5.20 \times 10^5$ | 18-19 | 0.5 ml/mouse | Healthy | 22-25 | Satisfactory |
| 20010816 | $5.20 \times 10^5$ | 18-19 | 0.5 ml/mouse | Healthy | 23-25 | Satisfactory |
| 20010511 | $1.00 \times 10^6$ | 18-20 | 0.5 ml/mouse | Healthy | 24-26 | Satisfactory |

Example 8

PIKA in Vaccine Composition Toxicity Study

The objective of this experiment is to validate the safety of the PIKA adjuvant.

The PIKA adjuvant (molecular weight 66,000 Daltons to 660,000 Daltons) was combined with hamster kidney cell inactivated purified rabies antigen (HKC-IPRA) in a ratio of PIKA:HKC-IPRA of 4:1.

The vaccine composition of PIKA and HKC-IPRA was compared with a commercially available inactivated purified rabies vaccine (IPRV) that included an alum adjuvant.

Mice were administered five (5) doses of the vaccine composition on day 0, day 3, day 7, day 14, and day 28. The dose administered was equivalent to approximately 300 times that of an adult human dose under the normal human rabies immunization regime.

Results of the toxicity observations are presented in table 7 below:

TABLE 7

Safety Observations after Administration of the Rabies Vaccine

| Formulations | Effect | Day 0 | Day 3 | Day 7 | Day 14 | Day 28 |
|---|---|---|---|---|---|---|
| HKC-IPRA plus PIKA | Allergy | 0/20 | 0/20 | 0/20 | 0/20 | 2/20 |
| HKC-IPRA plus PIKA | Death | 0/20 | 0/20 | 0/20 | 0/20 | 0/20 |
| IPRV (including Alum) | Allergy | 0/20 | 0/20 | 0/20 | 5/20 | — |

TABLE 7-continued

Safety Observations after Administration of the Rabies Vaccine

| Formulations | Effect | Day 0 | Day 3 | Day 7 | Day 14 | Day 28 |
|---|---|---|---|---|---|---|
| IPRV (including Alum) | Death | 0/20 | 0/20 | 0/20 | 2/20 | 7/20 |

Key: (Occurrence observed)/(Total number)

The conclusion drawn is that the PIKA/HKC-IPRA combination is safer than the commercially available IPRV.

Example 9

Safe Use of PIKA Adjuvant in Humans

In 2002, five (5) volunteers were immunized with a composition of PIKA (molecular weight 66,000 to 660,000 Daltons) and hamster kidney cell inactivated purified rabies antigen (HKC-IPRA). Volunteers were administered the vaccine composition on day 0, day 3, day 7, day 14, and day 30.

No local or systemic side effects were observed for any of the patients after each of the vaccinations.

The potency of the vaccine was measured using the standard NIH test with the results presented in table 8 below:

TABLE 8

Rabies Vaccine Potency Observations

| Day | ED50 | Neutralizing antibody IU/ml |
|---|---|---|
| 0 | 0 | 0 |
| 14 | >1.9 | >1.84 |
| 45 | 2.35 | 5.17 |

Results indicate that the vaccine composition of PIKA and HKC-IPRA induces a specific immune response and elicits the production of protective neutralizing antibodies.

Example 10

Post Exposure Test (Cell Mediated Immunity)

The post exposure test is the most definitive proof that the vaccine has the ability to eradicate pathogens from the host's body after infection. As such, it is an indication of the cell mediated immune response induced by the vaccine.

In the post exposure tests mice were infected with a wild strain of rabies virus and subsequently inoculated with: a hamster kidney cell inactivated purified rabies antigen (HKC-IPRA) in combination with PIKA adjuvant (molecular weight range from $1.65 \times 10^5$ to $1.2 \times 10^6$ Daltons), or HKC-IPRA in combination with an aluminum hydroxide (alum) adjuvant, a commercially available purified vero-cell rabies vaccine (PVRV), or phosphate buffer solution (PBS). Results conclusively show that the PIKA adjuvant improved survival rates, see table 9.

TABLE 9

Post Exposure Challenge Test

| Groups | Pre-determined 80% Death Dosage | Pre-determined 50% Death Dosage |
|---|---|---|
| 9.1 Death Rate After Treatment | | |
| PIKA plus HKC-IPRA | 2/20 | 0/20 |
| Alum plus HKC-IPRA | 10/20 | 9/20 |
| PVRV | 16/20 | 3/20 |
| Control (PBS) | 15/20 | 14/20 |
| 9.2 Survival Rate After Treatment | | |
| PIKA plus HKC-IPRA | 90.00% | 100.00% |
| Alum plus HKC-IPRA | 50.00% | 55.00% |
| PVRV | 20.00% | 85.00% |
| Control (PBS) | 25.00% | 30.00% |

Mice infected with a subcutaneous injection of live rabies virus were treated with vaccine at 6 hours, 1 day, 2 days, and 3 days after infection Example 11

Antigen Specific Cell Mediated Immune Response Interferon-Gamma Production

The production of interferon-gamma is an indicator of cell mediated immunity activity.

In this experiment, blood samples were taken from two trial patients and two control individuals. The volunteer patients had been vaccinated with the PIKA rabies vaccine, which contained PIKA (molecular weight range from 66,000 to 660,000 Daltons) and hamster kidney cell inactivated purified rabies antigen (HKC-IPRA) vaccine 2.5 years before collection of the blood samples.

Figure 2:
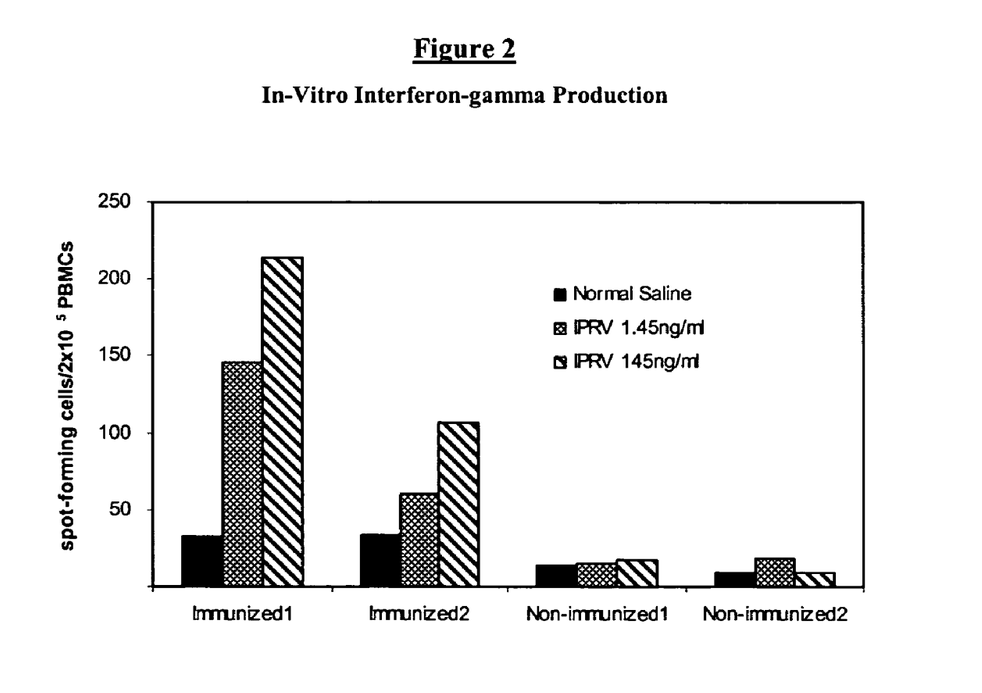
FIG. 2 shows that PIKA induces a dose dependent production of a specific interferon-gamma cytokine.

Results in FIG. 2 illustrate the significant difference in interferon-gamma produced by the two trial patients when compared with the control individuals.

The isolated monocytes from the blood samples were incubated with the same HKC-IPRA as was used in the original trial. After 3 days of incubation, the cell-free supernatants were harvested and the interferon-gamma in the supernatants was assayed by cytokine-specific ELISPOT. A dose dependant effect was observed.

The conclusions from the above observation are:
the rabies vaccine that included the PIKA adjuvant of the invention has the ability to induce the production of interferon-gamma and by implication to elicit a cell mediated immune response
the interferon-gamma response is specific (i.e., the response was directed to the rabies antigen as opposed to a non-specific reaction. If the interferon-gamma response were non-specific there would be no variation in the level of interferon-gamma production for the vaccinated patients' blood as the concentration of antigen stimulant increased Example 12

PIKA Efficacy Test

The object of this experiment is to demonstrate the PIKA's ability to elicit the production of interferon-gamma and interleukin 12 (IL-12).

Samples of splenocytes from normal healthy mice were incubated over a period of three days in the presence of PIKA (molecular weight range from 66,000 to 660,000) in a clean environment. At the end of the period the level of cytokines in the supernatants were assayed with IL-12(p40) and interferon-gamma specific ELISA tests. The results of the experiment are presented in the table 10 below:

TABLE 10

In-vitro Test for Cytokine Production

| PIKA ug/ml | IFN-gamma pg/ml | IL-12P40 pg/ml |
|---|---|---|
| 0 | 3 | 0 |
| 0.4 | 23 | 91 |
| 2 | 22 | 98 |
| 10 | 30 | 134 |
| 50 | 179 | 186 |
| 100 | 559 | N/A |
| 250 | 1340 | N/A |

The conclusion from the experiment above is that PIKA elicits a dose dependent production of interferon-gamma and IL-12 cytokines and as such induces a cell mediated immune response.

In a further experiment, four (4) mice were administered with 500 ug/mouse of PIKA (molecular weight range 66,000 to 660,000 Daltons) by peritoneal injection. A phosphate buffer solution was used as a negative control test. Five hours after injection a blood sample was withdrawn and a serum prepared. The level of cytokines in the serum were assayed with IL-12(p40) and interferon-gamma specific ELISA tests. The results of the experiment are presented in the table 11 below:

TABLE 11

Invivo Test for Cytokine Production

| Group | IFN-gamma pg/ml | IL-12P40 pg/ml |
|---|---|---|
| PBS | 4 | 2 |
| PIKA | 410 | 40 |

The conclusion from the experiment above is that PIKA is effective in stimulating a cell mediated immune response.

Example 13

Use of PIKA with Inactivated Purified Vero Cell Rabies Antigen

The objective of this experiment is to assess the effectiveness of PIKA in combination with an inactivated purified vero cell rabies vaccine (PVRV).

PIKA with a molecular weight range of 66,000 to 660,000 Daltons was combined with PVRV to form a rabies vaccine. The NIH test was used to evaluate the potency of the resulting vaccine composition. Results are presented in table 12 below:

TABLE 12

NIH Test Results for PIKA and Inactivated Purified Vero Cell Rabies Vaccine

| Vaccine Composition | Antigen | Adjuvant | Composition Potency (IU/ml) |
|---|---|---|---|
| PVRV | 0.02 IU/ml | n/a | 0.46 |
| PVRV plus PIKA | 0.02 IU/ml | PIKA | 3.68 |

The conclusion drawn is that PIKA enhances the potency of the inactivated purified vero cell rabies vaccine.

Example 14

Antigen Dose

This experiment demonstrates the requirement to have a minimum amount of hamster kidney cell inactivated purified rabies antigen (HKC-IPRA) present in the composition together with the PIKA adjuvant (molecular weight range from 66,000 to 660,000 Daltons) to trigger a substantially enhanced level of specific immune response.

Increased amounts of rabies antigen were added to a constant 0.1 mg of PIKA adjuvant. The potency was measured using the NIH standard Rabies Vaccine Potency Test. Following a predictable initial increase in potency, a distinct and dramatic increase was observed before the potency leveled off as expected with the addition of antigen (see table 13).

TABLE 13

Vaccine Potency with Increasing Amounts of Hamster Kidney Cell Inactivated Purified Rabies Antigen

| HKC-IPRA (IU) | HKC-IPRA plus 0.1 mg PIKA (IU) | Marginal Increase in Potency |
|---|---|---|
| 0.25 | 0.42 | — |
| 0.51 | 1.43 | 3.88 |
| 1.01 | 2.73 | 2.60 |
| 1.40 | 6.07 | 8.56 |
| 2.07 | 19.78 | 20.46 |
| 2.91 | 21.38 | 1.90 |

The marginal increase in potency is the increase in the potency of the HKC-IPRA/PIKA vaccine observed for the addition of one IU of the HKC-IPRA present.

The conclusion drawn is that a minimum presence of antigen is necessary before a substantive immune response is induced. Furthermore excessive antigen beyond that trigger point produces only a marginal incremental return in potency.

Example 15

Antigen Adjuvant Ratio

This experiment demonstrates the optimum mix of hamster kidney cell inactivated purified rabies antigen (HKC-IPRA) and the PIKA adjuvant (molecular weight range 66,000 to 660,000).

Various quantities of antigen were mixed with various quantities of adjuvant with PBS added to ensure a consistent overall volume. The potency of the resulting vaccines was determined using the NIH potency test. The findings are presented in table 14.

Consideration of the combined test results indicates that the optimum vaccine combination is a ratio of PIKA to antigen in the range of at least 3 to 1.

TABLE 14

Rabies Vaccine Potency at Various Antigen to Adjuvant Ratios

| Samples | HKC-IPRA (ml) | PIKA (ml) | PBS (ml) | Ratio (PIKA:HKC-IPRA) | ED50 | Potency (IU/ml) |
|---|---|---|---|---|---|---|
| A | 0.20 | 0.80 | — | 4.0 to 1 | 2.65 | 7.84 |
| B | 0.20 | 0.70 | 0.10 | 3.5 to 1 | 2.46 | 5.20 |
| C | 0.20 | 0.60 | 0.20 | 3.0 to 1 | 2.40 | 4.22 |
| D | 0.20 | — | 0.80 | 0 to 1 | 1.85 | 1.43 |
| Standard | | | na | na | 2.52 | 6.70 |

Example 16

Freeze-Dried Storage of PIKA and PIKA Combined with Rabies Vaccine

This example demonstrates that PIKA is stable in a freeze-dried form.

Freeze-dried technology has been used for long term storage of rabies vaccines for up to three years. The inventor sought to test whether freeze-dried storage of PIKA (of molecular weight range from 66,000 to 660,000) and rabies vaccines containing PIKA would be beneficial. The following compositions were used for the freeze-dried storage test: i) unfrozen PIKA added to a reconstituted freeze-dried hamster kidney cell inactivated purified rabies antigen (HKC-IPRA), ii) reconstituted freeze-dried composition of PIKA plus HKC-IPRA, iii) a reconstituted freeze-dried commercial rabies vaccine (no added PIKA) and iv) an unfrozen commercial rabies vaccine. Table 15 shows that freeze-dried PIKA and PIKA-containing rabies vaccines were ideal for long term storage of rabies vaccines.

TABLE 15

Effects of Freeze-dried Storage on the Potency of Rabies Vaccines

| Sample | ED50 | Relative Potency | IU/ml |
|---|---|---|---|
| i) PIKA-diluted freeze-dried rabies vaccine | 2.89 | 2.34 | 15.71 |
| ii) PBS-diluted freeze-dried PIKA-containing rabies vaccine | 3.00 | 3.00 | 20.23 |
| iii) PBS-diluted freeze-dried commercial rabies vaccine | 1.85 | 0.21 | 1.43 |
| iv) Standard Rabies vaccine unfrozen | 2.52 | 1.00 | 6.70 |

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. A polynucleotide adjuvant composition comprising:
a polyriboinosinic-polyribocytidylic acid (PIC),
an antibiotic, and
a positive ion,
wherein the composition is suitable for use in humans and contains polynucleotide adjuvant composition molecules heterogeneous for at least one of molecular weight or size, wherein the molecular weight is in a molecular weight range of from 338,000 to 1,200,000 Daltons and wherein the size is in a molecular size range of from 13.5 to 24.0 Svedbergs.

2. A polynucleotide adjuvant composition comprising:
a polyriboinosinic-polyribocytidylic acid (PIC),
an antibiotic, and
a positive ion,
wherein the composition is suitable for use in humans and contains polynucleotide adjuvant composition molecules that have an average molecular weight greater than 338,000 Daltons or have an average molecular size greater than 13.5 Svedbergs.

3. The polynucleotide adjuvant composition of claim 2, wherein the average molecular weight is equal to or greater than 500,000 Daltons or the average molecular size is equal to or greater than 15 Svedbergs.

4. The polynucleotide adjuvant composition of any of claims 1, 2 or 3, wherein the antibiotic is kanamycin, neomycin, an anthracycline, butirosin sulfate, a gentamicin, hygromycin, amikacin, dibekacin, nebramycin, metrzamide, puromycin, streptomycin, or streptozocin.

5. The polynucleotide adjuvant composition of any of claims 1, 2 or 3, wherein the antibiotic is kanamycin, neomycin, an anthracycline, butirosin sulfate, a gentamicin, hygromycin, amikacin, dibekacin, nebramycin, metrzamide, puromycin, streptomycin, or streptozocin and the positive ion is calcium, cadmium, lithium, magnesium, cerium, cesium, chromium, cobalt, deuterium, gallium, iodine, iron, or zinc; and wherein the positive ion is the form of an inorganic salt or an organic complex.

6. The polynucleotide adjuvant composition of any of claims 1, 2 or 3, wherein the antibiotic is kanamycin, neomycin, an anthracycline, butirosin sulfate, a gentamicin, hygromycin, amikacin, dibekacin, nebramycin, metrzamide, puromycin, streptomycin, or streptozocin and the source of positive ions is calcium chloride, calcium carbonate, calcium fluoride, calcium hydroxide, calcium phosphates, or calcium sulfate.

7. The polynucleotide adjuvant composition of any of claims 1, 2 or 3, wherein the antibiotic is kanamycin sulfate and the positive ion is provided by calcium chloride.

8. A kit comprising the polynucleotide adjuvant composition of any of claims 1, 2 or 3 and an antigenic compound, wherein the antibiotic is kanamycin sulfate and the positive ion is provided by calcium chloride.

9. A method for enhancing an immune response to an antigenic compound, comprising: administering to a subject a composition comprising an antigenic compound and the polynucleotide adjuvant composition of any of claims 1, 2 or 3, wherein the antibiotic is kanamycin sulfate and the positive ion is provided by calcium chloride.

10. The method of claim 9, wherein said administering is by parenteral injection, intramuscular injection, intraperitoneal injection, intravenous injection, subcutaneous injection, inhalation, rectal delivery, vaginal delivery, nasal delivery, oral delivery, opthamalic delivery, topical delivery, transdermal delivery or intradermal delivery.

11. The polynucleotide adjuvant composition of claim 4, wherein the antibiotic is kanamycin.

12. The polynucleotide adjuvant composition of any of claims 1, 2 or 3, wherein the positive ion is calcium, cadmium, lithium, magnesium, cerium, cesium, chromium, cobalt, deuterium, gallium, iodine, iron, or zinc.

13. The polynucleotide adjuvant composition of claim 12, wherein the positive ion is calcium.

14. An immunogenic composition, comprising:
a polynucleotide adjuvant composition comprising a polyriboinosinic-polyribocytidylic acid (PIC), an antibiotic, and a positive ion; and
an antigenic compound;
wherein the composition is suitable for use in humans and contains polynucleotide adjuvant composition molecules that have an average molecular weight greater than 338,000 Daltons or have an average molecular size greater than 13.5 Svedbergs.

15. The immunogenic composition of claim 14, wherein the antibiotic is kanamycin sulfate and the positive ion is provided by calcium chloride.

16. The immunogenic composition of claim 14, wherein the antigenic compound is a human antigen, a non-human animal antigen, a plant antigen, bacterial antigen, a fungal antigen, a viral antigen, a parasite antigen, or a cancer antigen.

17. The immunogenic composition of claim 16, wherein the viral antigen is a rabies antigen.

18. The immunogenic composition of claim 17, wherein the rabies antigen is an inactivated purified rabies antigen.

19. The immunogenic composition of claim 14, wherein polynucleotide adjuvant composition is capable of eliciting an enhanced specific humoral and/or cell mediated immune response.

20. The immunogenic composition of claim 14, wherein at least one of the adjuvant composition or the immunogenic composition is in a solid form or a liquid form, wherein the liquid form is a solution or a suspension.

21. The immunogenic composition of claim 14, wherein at least one of the adjuvant composition or the immunogenic composition is freeze-dried.

22. An immunogenic composition, comprising:
a polynucleotide adjuvant composition comprising a polyriboinosinic-polyribocytidylic acid (PIC), an antibiotic, and a positive ion, wherein the antibiotic is kanamycin and the positive ion is calcium; and
an antigenic compound;
wherein the composition is suitable for use in humans and contains polynucleotide adjuvant composition molecules that have an average molecular weight greater than 338,000 Daltons or have an average molecular size greater than 13.5 Svedbergs.

23. The immunogenic composition of claim 22, wherein the antigenic compound is a human antigen, a non-human animal antigen, a plant antigen, bacterial antigen, a fungal antigen, a viral antigen, a parasite antigen, or a cancer antigen.

24. The immunogenic composition of claim 23, wherein the viral antigen is a rabies antigen.

25. The immunogenic composition of claim 24, wherein the rabies antigen is an inactivated purified rabies antigen.

26. The immunogenic composition of claim 22, wherein polynucleotide adjuvant composition is capable of eliciting an enhanced specific humoral and/or cell mediated immune response.

27. The immunogenic composition of claim 22, wherein at least one of the adjuvant composition or the immunogenic composition is in a solid form or a liquid form, wherein the liquid form is a solution or a suspension.

28. The immunogenic composition of claim 22, wherein at least one of the adjuvant composition or the immunogenic composition is freeze-dried.

29. An immunogenic composition, comprising:
a polynucleotide adjuvant composition comprising a polyriboinosinic-polyribocytidylic acid (PIC), an antibiotic, and a positive ion; and
an antigenic compound;
wherein the composition is suitable for use in humans and contains polynucleotide adjuvant composition molecules heterogeneous for at least one of molecular weight or size, wherein the molecular weight is in a molecular weight range of from 338,000 to 1,200,000 Daltons and wherein the size is in a molecular size range of from 13.5 to 24.0 Svedberg.

30. The immunogenic composition of claim 29, wherein the antibiotic is kanamycin sulfate and the positive ion is provided by calcium chloride.

31. The immunogenic composition of claim 29, wherein the antigenic compound is a human antigen, a non-human animal antigen, a plant antigen, bacterial antigen, a fungal antigen, a viral antigen, a parasite antigen, or a cancer antigen.

32. The immunogenic composition of claim 31, wherein the viral antigen is a rabies antigen.

33. The immunogenic composition of claim 32, wherein the rabies antigen is an inactivated purified rabies antigen.

34. The immunogenic composition of claim 29, wherein polynucleotide adjuvant composition is capable of eliciting an enhanced specific humoral and/or cell mediated immune response.

35. The immunogenic composition of claim 29, wherein at least one of the adjuvant composition or the immunogenic composition is in a solid form or a liquid form, wherein the liquid form is a solution or a suspension.

36. The immunogenic composition of claim 29, wherein at least one of the adjuvant composition or the immunogenic composition is freeze-dried.

37. A method for enhancing an immune response to an antigenic compound, comprising: administering to a subject the immunogenic composition of claims 14, 22 or 29, wherein the antibiotic is kanamycin sulfate and the positive ion is provided by calcium chloride.

38. The method of claim 37, wherein said administering is by parenteral injection, intramuscular injection, intraperitoneal injection, intravenous injection, subcutaneous injection, inhalation, rectal delivery, vaginal delivery, nasal delivery, oral delivery, opthamalic delivery, topical delivery, transdermal delivery or intradermal delivery.

* * * * *